(12) United States Patent
Liu et al.

(10) Patent No.: US 10,954,550 B2
(45) Date of Patent: Mar. 23, 2021

(54) METHOD AND SYSTEM FOR SCREENING NANOBODY

(71) Applicant: BGI Shenzhen Co., Limited, Shenzhen (CN)

(72) Inventors: Xiao Liu, Shenzhen (CN); Chao Nie, Shenzhen (CN); Wei Zhang, Shenzhen (CN); Zhe Ren, Shenzhen (CN); Ruifang Zhang, Shenzhen (CN); Xiaojing Zeng, Shenzhen (CN); Xinyang Li, Shenzhen (CN); Naibo Yang, Shenzhen (CN)

(73) Assignee: BGI SHENZHEN, Shenzhen (CN)

( * ) Notice: Subject to any disclaimer, the term of this patent is extended or adjusted under 35 U.S.C. 154(b) by 673 days.

(21) Appl. No.: 15/502,438

(22) PCT Filed: Aug. 6, 2015

(86) PCT No.: PCT/CN2015/086253
§ 371 (c)(1),
(2) Date: Feb. 7, 2017

(87) PCT Pub. No.: WO2016/019888
PCT Pub. Date: Feb. 11, 2016

(65) Prior Publication Data
US 2017/0226566 A1 Aug. 10, 2017

(30) Foreign Application Priority Data
Aug. 7, 2014 (CN) .......................... 201410386936.2

(51) Int. Cl.
| | |
|---|---|
| *G01N 33/48* | (2006.01) |
| *G01N 33/50* | (2006.01) |
| *C12Q 1/6811* | (2018.01) |
| *C07K 16/00* | (2006.01) |
| *C12N 15/10* | (2006.01) |
| *C12Q 1/6844* | (2018.01) |
| *C40B 40/10* | (2006.01) |
| *B01D 15/38* | (2006.01) |
| *C12Q 1/6806* | (2018.01) |
| *C40B 50/06* | (2006.01) |

(52) U.S. Cl.
CPC ............ *C12Q 1/6811* (2013.01); *C07K 16/00* (2013.01); *C07K 16/005* (2013.01); *C12N 15/1034* (2013.01); *C12Q 1/6844* (2013.01); *C40B 40/10* (2013.01); *B01D 15/3809* (2013.01); *C07K 2317/22* (2013.01); *C07K 2317/56* (2013.01); *C07K 2317/569* (2013.01); *C12Q 1/6806* (2013.01); *C40B 50/06* (2013.01)

(58) Field of Classification Search
None
See application file for complete search history.

(56) References Cited

U.S. PATENT DOCUMENTS

| | | | | |
|---|---|---|---|---|
| 2005/0161399 | A1* | 7/2005 | Dillon | C07K 1/023 210/635 |
| 2006/0211088 | A1* | 9/2006 | Hermans | C07K 16/00 435/69.1 |

FOREIGN PATENT DOCUMENTS

| | | | | |
|---|---|---|---|---|
| CN | 102219853 A | 10/2011 | | |
| CN | 103866401 A | 6/2014 | | |
| WO | WO-2011008349 A2 * | 1/2011 | ........... | C12Q 1/6883 |
| WO | WO-2012178083 A1 * | 12/2012 | ............. | A61K 38/12 |

OTHER PUBLICATIONS

Tillib, S.V. et al., "Fingerprint-like Analysis of 'Nanoantibody' Selection by Phage Display Using Two Helper Phage Variants", Acta Naturae, vol. 2, No. 3, Jun. 30, 2010.
International Search Report issued for PCT/CN2015/086253, dated Nov. 20, 2015.
Written Opinion of the International Searching Authority issued for PCT/CN2015/086253, dated Nov. 20, 2015.
Office Action issued in CN Application No. 201580042224.1, dated Feb. 3, 2020.
Zhu, Jiang et al., "De novo identification of YRC01-class HIV-1 broadly neutralizing antibodies by next-generation sequencing analysis of B cell transcripts" Proceedings of the National Academy of Sciences of the United States of America, Oct. 2013, 110(43), E4088-E4097.
Scheid, Johannes F., et al., "Sequence and Structural Convergence of Broad and Potent HIV Antibodies that Mimic CD4 Binding" Science vol. 333, Sep. 16, 2011, pp. 1633-1637.
DeKosky, Brandon J., et al., "High-throughput sequencing of the paired human immunoglobulin heavy and light chain repertoire" Nature Biotechnology vol. 31, No. 2., (Feb. 2013), pp. 166-171.
Office Action issued in CN Application No. 201580042224.1, dated Aug. 20, 2020.
Boutz, D. R. et al. "Proteomic Identification of Monoclonal Antibodies from Serum" (2014) Analytical Chemistry 86:4758-4766.
Cheung, W. C., et al. "A proteomics approach for the identification and cloning of monoclonal antibodies from serum" Nature Biotechnology (2012) 30(5): 447-452.

* cited by examiner

*Primary Examiner* — Russell S Negin
(74) *Attorney, Agent, or Firm* — Westman, Champlin & Koehler, P.A.; Z. Peter Sawicki; Amanda M. Prose

(57) ABSTRACT

Provided are a method for screening for nanobodies and a corresponding system. The method uses polymerase chain reactions and cDNA 5' end rapid amplification technology to screen for and obtain nanobodies. The experiment cycle requires only approximately 21 days.

14 Claims, 12 Drawing Sheets
Specification includes a Sequence Listing.

SEQUENCE LISTING

```
<160> NUMBER OF SEQ ID NOS: 23

<210> SEQ ID NO 1
<211> LENGTH: 105
<212> TYPE: DNA
<213> ORGANISM: Camelus bactrianus

<400> SEQUENCE: 1
aacccaagat accccaacca caaccaaaac cacaaccaca accacaacca caaccaaaac    60
cacaaccaaa acctgaacca gaatgcacgt gtcccaaatg tccag                    105

<210> SEQ ID NO 2
<211> LENGTH: 36
<212> TYPE: DNA
<213> ORGANISM: Camelus bactrianus

<400> SEQUENCE: 2
ggaacgaatg aagtatgcaa gtgtcccaaa tgtcca                              36

<210> SEQ ID NO 3
<211> LENGTH: 23
<212> TYPE: DNA
<213> ORGANISM: Artificial
<220> FEATURE:
<223> OTHER INFORMATION: primer

<400> SEQUENCE: 3
ggtacgtgct gttgaactgt tcc                                            23

<210> SEQ ID NO 4
<211> LENGTH: 18
<212> TYPE: DNA
<213> ORGANISM: Artificial
<220> FEATURE:
<223> OTHER INFORMATION: primer

<400> SEQUENCE: 4
agaccaggca gccgaarg                                                  18

<210> SEQ ID NO 5
<211> LENGTH: 19
<212> TYPE: DNA
<213> ORGANISM: Artificial
<220> FEATURE:
<223> OTHER INFORMATION: primer

<400> SEQUENCE: 5
ggagtggact tgggctgac                                                 19

<210> SEQ ID NO 6
<211> LENGTH: 19
<212> TYPE: DNA
```

```
<213> ORGANISM: Artificial
<220> FEATURE:
<223> OTHER INFORMATION: primer

<400> SEQUENCE: 6
tgagggtgta gccttgggt                                                    19

<210> SEQ ID NO 7
<211> LENGTH: 19
<212> TYPE: DNA
<213> ORGANISM: Artificial
<220> FEATURE:
<223> OTHER INFORMATION: primer

<400> SEQUENCE: 7
aarcacacga ytgaggcac                                                    19

<210> SEQ ID NO 8
<211> LENGTH: 30
<212> TYPE: DNA
<213> ORGANISM: Artificial
<220> FEATURE:
<223> OTHER INFORMATION: primer

<400> SEQUENCE: 8
ggccacgcgt cgactagtac gggggggggg                                        30

<210> SEQ ID NO 9
<211> LENGTH: 25
<212> TYPE: DNA
<213> ORGANISM: Artificial
<220> FEATURE:
<223> OTHER INFORMATION: primer

<400> SEQUENCE: 9
ctctgctcct tctcaccctc ctcac                                             25

<210> SEQ ID NO 10
<211> LENGTH: 21
<212> TYPE: DNA
<213> ORGANISM: Artificial
<220> FEATURE:
<223> OTHER INFORMATION: primer

<400> SEQUENCE: 10
tcagaggacg gcgggaacag g                                                 21

<210> SEQ ID NO 11
<211> LENGTH: 132
<212> TYPE: PRT
<213> ORGANISM: Artificial
<220> FEATURE:
<223> OTHER INFORMATION: antibody 1

<400> SEQUENCE: 11

Met Ala His Val Gln Leu Val Glu Ser Gly Gly Gly Ala Val Gln Thr
1               5                   10                  15

Gly Gly Ser Leu Arg Leu Thr Cys Thr Ala Val Gly Leu Thr Phe Glu
            20                  25                  30

Gly Gly Asn Gln Gly Trp Tyr Arg Glu Thr Pro Gly Asn Glu Phe Glu
        35                  40                  45

Leu Val Ser Ser Ile Ala Pro Asp Gly Ser Arg Trp Tyr Ala Asp Ser
    50                  55                  60

Val Gln Gly Arg Phe Thr Ile Ser Arg Asn Val Leu Pro Glu Arg Leu
```

```
                65                  70                  75                  80
Ser Leu Gln Met Thr Arg Leu Lys Ala Glu Asp Thr Ala Met Tyr Tyr
                    85                  90                  95

Cys Ala Ala Gly Pro Asp Val Gly Arg Glu Lys His Leu Thr Ala Asp
                100                 105                 110

Gln Val Leu Ser Ile Arg Arg Asn Asn Phe Trp Gly Gln Gly Thr Gln
            115                 120                 125

Val Thr Val Ser
        130

<210> SEQ ID NO 12
<211> LENGTH: 119
<212> TYPE: PRT
<213> ORGANISM: Artificial
<220> FEATURE:
<223> OTHER INFORMATION: antibody 2

<400> SEQUENCE: 12

Met Ala His Val Gln Leu Val Glu Ser Gly Gly Gly Ser Val Gln Thr
1               5                   10                  15

Gly Gly Ser Leu Arg Leu Ser Cys Lys Pro Ser Phe Phe Ile Leu Asp
            20                  25                  30

Asp Phe Asp Met Met Trp Tyr Arg Gln Ala Pro Gly Asn Glu Cys Glu
        35                  40                  45

Leu Val Ser Ser Ile Ser Gly Asp Gly Ser Thr Tyr Tyr Thr Asp Ala
    50                  55                  60

Val Lys Gly Arg Phe Thr Ile Ser His Asp Asn Ala Lys Asn Ser Val
65                  70                  75                  80

Asp Leu Gln Met Asn Ser Leu Lys Pro Asp Asp Thr Ala Val Tyr Tyr
                    85                  90                  95

Cys Ala Ala Thr Gly Gln Met Leu Ser Val Ala Gly Cys Arg Thr Gln
                100                 105                 110

Gly Thr Gln Val Thr Val Ser
            115

<210> SEQ ID NO 13
<211> LENGTH: 119
<212> TYPE: PRT
<213> ORGANISM: Artificial
<220> FEATURE:
<223> OTHER INFORMATION: antibody 3

<400> SEQUENCE: 13

Met Ala Asp Val Gln Leu Val Glu Ser Gly Gly Gly Ser Val Gln Thr
1               5                   10                  15

Gly Gly Ser Leu Arg Leu Ser Cys Lys Pro Ser Phe Phe Ile Leu Asp
            20                  25                  30

Asp Phe Asp Met Met Trp Tyr Arg Gln Ala Pro Gly Asn Glu Cys Glu
        35                  40                  45

Leu Val Ser Ser Ile Ser Gly Asp Gly Ser Thr Tyr Tyr Thr Asp Ala
    50                  55                  60

Val Lys Gly Arg Phe Thr Ile Ser His Asp Asn Ala Lys Asn Ser Val
65                  70                  75                  80

Asp Leu Gln Met Asn Ser Leu Lys Pro Asp Asp Thr Ala Val Tyr Tyr
                    85                  90                  95

Cys Ala Ala Thr Gly Gln Met Leu Ser Val Ala Gly Cys Arg Thr Gln
                100                 105                 110
```

Gly Thr Gln Val Thr Val Ser
        115

<210> SEQ ID NO 14
<211> LENGTH: 125
<212> TYPE: PRT
<213> ORGANISM: Artificial
<220> FEATURE:
<223> OTHER INFORMATION: antibody 4

<400> SEQUENCE: 14

Met Ala His Val Gln Leu Val Glu Ser Gly Gly Ser Val Gln Ala
1               5                   10                  15

Gly Gly Ser Leu Ser Leu Ser Cys Ala Thr Arg Gly Tyr Thr Arg Arg
            20                  25                  30

Ser Gly Cys Leu Ala Trp Phe Arg Gln Val Pro Gly Lys Glu Arg Glu
            35                  40                  45

Met Val Ala Gln Ile Gln Asp Asp Gly Ala Lys His Tyr Asp Ser Thr
    50                  55                  60

Ala Glu Gly Arg Phe Thr Ile Ser Lys Asp Ala Ala Lys Asp Thr Leu
65                  70                  75                  80

Asp Leu Arg Met Thr Ser Leu Lys Pro Glu Asp Ser Gly Met Tyr Tyr
                85                  90                  95

Cys Ala Val Asp Gly Pro Val Ala Phe Cys Ser Asp Tyr Pro Ser Asp
                100                 105                 110

Phe Arg Gly Trp Gly Gln Gly Thr Gln Val Thr Val Ser
            115                 120                 125

<210> SEQ ID NO 15
<211> LENGTH: 132
<212> TYPE: PRT
<213> ORGANISM: Artificial
<220> FEATURE:
<223> OTHER INFORMATION: antibody 5

<400> SEQUENCE: 15

Met Ala Asp Val Gln Leu Val Glu Ser Gly Gly Gly Ala Val Gln Thr
1               5                   10                  15

Gly Gly Ser Leu Arg Leu Thr Cys Thr Ala Val Gly Leu Thr Phe Glu
            20                  25                  30

Gly Gly Asn Gln Gly Trp Tyr Arg Glu Thr Pro Gly Asn Glu Phe Glu
            35                  40                  45

Leu Val Ser Ser Ile Ala Pro Asp Gly Ser Arg Trp Tyr Ala Asp Ser
    50                  55                  60

Val Gln Gly Arg Phe Thr Ile Ser Arg Asn Val Leu Pro Glu Arg Leu
65                  70                  75                  80

Ser Leu Gln Met Thr Arg Leu Lys Ala Glu Asp Thr Ala Met Tyr Tyr
                85                  90                  95

Cys Ala Ala Gly Pro Asp Val Gly Arg Glu Lys His Leu Thr Ala Asp
                100                 105                 110

Gln Val Leu Ser Ile Arg Arg Asn Asn Phe Trp Gly Gln Gly Thr Gln
            115                 120                 125

Val Thr Val Ser
        130

<210> SEQ ID NO 16
<211> LENGTH: 55
<212> TYPE: PRT
<213> ORGANISM: Artificial

```
<220> FEATURE:
<223> OTHER INFORMATION: antibody 6

<400> SEQUENCE: 16

Val Lys Gly Arg Phe Thr Ile Ser His Asp Asn Ala Lys Asn Ser Val
1               5                   10                  15

Asp Leu Gln Met Asn Ser Leu Lys Pro Asp Asp Thr Ala Val Tyr Tyr
            20                  25                  30

Cys Ala Ala Thr Gly Gln Met Leu Ser Val Ala Gly Cys Arg Thr Gln
        35                  40                  45

Gly Thr Gln Val Thr Val Ser
    50                  55

<210> SEQ ID NO 17
<211> LENGTH: 123
<212> TYPE: PRT
<213> ORGANISM: Artificial
<220> FEATURE:
<223> OTHER INFORMATION: antibody 7

<400> SEQUENCE: 17

Met Ala His Val Gln Leu Val Glu Ser Gly Gly Gly Val Gln Ala
1               5                   10                  15

Gly Gly Ser Leu Lys Leu Ser Cys Ala Gly Ser Ala Tyr Ile Leu Glu
            20                  25                  30

Asn Cys Gly Met Val Trp Tyr Arg Gln Thr Lys Gly Lys Glu Glu Lys
        35                  40                  45

Leu Val Ser Val Arg Lys Asp Gly Thr Pro Val Tyr Glu Asp Thr Val
    50                  55                  60

Lys Gly Arg Phe Thr Leu Ser His Asp Arg Ser Lys Asn Thr Met Tyr
65                  70                  75                  80

Leu Gln Met Asp Asn Leu Lys Thr Glu Asp Thr Gly Val Tyr Tyr Cys
                85                  90                  95

Ala Ala Leu Asn Ser Thr Tyr Gly Gly Arg Phe Gly Trp Cys Lys Asp
            100                 105                 110

Phe Arg Gly Gln Gly Thr Gln Val Thr Val Ser
        115                 120

<210> SEQ ID NO 18
<211> LENGTH: 123
<212> TYPE: PRT
<213> ORGANISM: Artificial
<220> FEATURE:
<223> OTHER INFORMATION: antibody 8

<400> SEQUENCE: 18

Met Ala His Val Gln Leu Val Glu Ser Gly Gly Gly Ser Val Gln Ala
1               5                   10                  15

Gly Gly Ser Leu Lys Leu Thr Cys Ala Gly Ser Ala Tyr Ile Leu Glu
            20                  25                  30

Gln Cys Gly Met Gly Trp Phe Arg Gln Ala Pro Gly Lys Glu Glu Asn
        35                  40                  45

Leu Val Ser Leu Arg Arg Asp Gly Thr Val Tyr Ser Asp Ser Val
    50                  55                  60

Lys Gly Arg Phe Thr Ile Ser Gln Asp Arg Thr Lys Asn Ile Leu Tyr
65                  70                  75                  80

Leu Gln Met Asn Asp Leu Lys Asp Glu Asp Thr Gly Met Tyr Tyr Cys
                85                  90                  95
```

Ala Ala Leu Asn Ser Ser Gly Gly Arg Phe Ala Trp Cys Ser Asp
            100                 105                 110

Phe Arg Gly Gln Gly Thr Gln Val Thr Val Ser
            115                 120

<210> SEQ ID NO 19
<211> LENGTH: 136
<212> TYPE: PRT
<213> ORGANISM: Artificial
<220> FEATURE:
<223> OTHER INFORMATION: antibody 9

<400> SEQUENCE: 19

Met Ala His Val Gln Leu Val Glu Ser Gly Gly Gly Ser Val Gln Ala
1               5                   10                  15

Gly Gly Ser Leu Arg Leu Ser Cys Ala Ile Ser Gly Arg Ser Asn Glu
            20                  25                  30

Asn Tyr Phe Leu Ala Trp Phe Arg Gln Pro Pro Gly Lys Glu Arg Glu
        35                  40                  45

Gly Val Ala Ala Met Tyr Thr Gly Phe Gly Gly Asn Ile Tyr Tyr
    50                  55                  60

Asp Asp Ser Val Lys Gly Arg Phe Thr Ile Ser Gln Asp Asn Ser Lys
65                  70                  75                  80

Asn Thr Leu Phe Leu Gln Met Asn Val Leu Arg Pro Glu Asp Thr Ala
                85                  90                  95

Met Tyr Tyr Cys Ala Ala Arg Lys Val Ala Arg Gly Ser His Phe Ser
            100                 105                 110

Leu Gly Arg Ala Pro Ala Leu Arg Arg Asp Glu Tyr Asn Phe Trp Gly
            115                 120                 125

Gln Gly Thr Gln Val Thr Val Ser
        130                 135

<210> SEQ ID NO 20
<211> LENGTH: 124
<212> TYPE: PRT
<213> ORGANISM: Artificial
<220> FEATURE:
<223> OTHER INFORMATION: antibody 10

<400> SEQUENCE: 20

Met Ala His Val Gln Leu Val Glu Ser Gly Gly Gly Ser Val Gln Ala
1               5                   10                  15

Gly Gly Ser Leu Arg Leu Ser Cys Thr His Ser Gly Tyr Ile Ser Ser
            20                  25                  30

Arg His Cys Met Gly Trp Phe Arg Gln Ala Pro Gly Lys Ala Arg Glu
        35                  40                  45

Gly Ile Ala Gly Ile Arg Arg Asp Gly Asp Glu Tyr Tyr Ala Gly Ser
    50                  55                  60

Val Lys Gly Arg Phe Thr Ile Ser Gln Asp Asn Ala Lys Asn Ile Ile
65                  70                  75                  80

Tyr Leu Gln Met Ser Ser Leu Thr Pro Asp Asp Thr Ala Met Tyr Tyr
                85                  90                  95

Cys Ala Ala Gly Thr Arg Ile Ile Val Gly Asp Tyr Cys Asp Gly Ile
            100                 105                 110

Thr Thr Trp Gly Gln Gly Thr Gln Val Thr Val Ser
            115                 120

<210> SEQ ID NO 21

<211> LENGTH: 125
<212> TYPE: PRT
<213> ORGANISM: Artificial
<220> FEATURE:
<223> OTHER INFORMATION: C10WBA-IgG23_26

<400> SEQUENCE: 21

Met Ala His Val Gln Leu Val Glu Ser Gly Gly Gly Ser Val Gln Ala
1               5                   10                  15

Gly Gly Ser Leu Lys Leu Ser Cys Ala Val Ser Pro Tyr Ile Phe Thr
            20                  25                  30

Arg Cys Gly Leu Gly Trp Tyr Arg Gln Ala Pro Gly Asn Val Arg Glu
        35                  40                  45

Leu Val Ser Ser Met Asp Ser Asp Gly Thr Thr Ile Tyr Ala Asp Ser
    50                  55                  60

Val Lys Gly Arg Phe Thr Ile Ser Gln Asp Asn Glu Lys Asn Met Leu
65                  70                  75                  80

Tyr Leu Gln Met Asn Ser Leu Lys Thr Glu Asp Thr Ala Met Tyr Tyr
                85                  90                  95

Cys Ala Ala Asp His Gln Asp Pro Ser Arg Gly Ala Tyr Phe Asp His
            100                 105                 110

Cys Asn Tyr Met Gly Gln Gly Thr Gln Val Thr Val Ser
        115                 120                 125

<210> SEQ ID NO 22
<211> LENGTH: 141
<212> TYPE: PRT
<213> ORGANISM: Artificial
<220> FEATURE:
<223> OTHER INFORMATION: C10WBA-IgG23_1064

<400> SEQUENCE: 22

Met Ala Asp Val Gln Leu Val Glu Ser Gly Gly Gly Leu Val Gln Pro
1               5                   10                  15

Gly Gly Ser Leu Arg Leu Ser Cys Val Gly Ser Gly Phe Gly Pro Lys
            20                  25                  30

Val Tyr Cys Met Gly Trp Phe Arg Gln Ala Pro Gly Lys Glu Arg Glu
        35                  40                  45

Gly Val Ala Ala Val Asp Ser Glu Gly Asn Thr Ser Tyr Val Glu Ser
    50                  55                  60

Val Lys Gly Arg Phe Thr Ile Ser Gln Asp Lys Asp Lys Asn Thr Val
65                  70                  75                  80

Tyr Leu Glu Met Asn Asn Leu Lys Pro Glu Asp Thr Ala Met Tyr Tyr
                85                  90                  95

Cys Ala Ala Glu Leu Gln Ile Pro Leu Asn Arg Gln Val Ala Gly Arg
            100                 105                 110

Ser Trp His Cys Pro Leu Leu Ala Pro Val Ser Ala Gly Gly Arg His
        115                 120                 125

Ser Gly Val Trp Gly Gln Gly Thr Gln Val Thr Val Ser
    130                 135                 140

<210> SEQ ID NO 23
<211> LENGTH: 134
<212> TYPE: PRT
<213> ORGANISM: Artificial
<220> FEATURE:
<223> OTHER INFORMATION: C10WBA-IgG23_666

<400> SEQUENCE: 23

-continued

```
Met Ala Asp Val Gln Leu Val Glu Ser Gly Gly Ser Val Gln Ala
1               5                   10                  15

Gly Gly Ser Leu Arg Leu Ser Cys Ser Ile Ser Pro Ala Ile Ser His
            20                  25                  30

Arg Asn Cys Met Ala Trp Phe Arg Gln Val Pro Gly Asn Glu Arg Glu
        35                  40                  45

Gly Val Ala Ala Ile Tyr Leu Thr Ala Gly Ala Thr His Tyr Ile Asp
    50                  55                  60

Ser Val Lys Gly Arg Phe Thr Ile Ser Glu Asp Ser Ala Glu Asn Thr
65                  70                  75                  80

Met Tyr Leu Gln Met Glu Asn Leu Lys Ser Glu Asp Thr Gly Met Tyr
                85                  90                  95

Tyr Cys Ala Ala Asp Phe Phe Pro Phe Lys Gly Gly Ala Ala Ser Leu
                100                 105                 110

Ala Pro Met Cys Leu Asn Gly Leu Glu Tyr Arg His Arg Gly Gln Gly
            115                 120                 125

Thr Gln Val Thr Val Ser
    130
```

METHOD AND SYSTEM FOR SCREENING NANOBODY

CROSS-REFERENCE TO RELATED APPLICATION

This application is the U.S. national phase of PCT Application No. PCT/CN2015/086253 filed on Aug. 6, 2015, which claims a priority to and benefits of Chinese Patent Application Serial No. 201410386936.2, filed with the State Intellectual Property Office of P. R. China on Aug. 7, 2014, the entire contents of which are incorporated herein by reference.

FIELD

The present disclosure relates to the field of biotechnology, specifically to method and system for screening nanobody.

BACKGROUND

It has been long recognized that an antibody is generally composed of a light chain and a heavy chain in pairs, containing a complete constant region including CH1, CH2, CH3 and the like, i.e. the so-called traditional antibody. However, Hamers-Casterman et al. found a heavy chain antibody (HCAb) naturally existing in serum of a Camelidae animal in 1993, which contains the heavy chain only, but no light chain. Cloning a variable domain of the heavy chain antibody (HCAbs) will result in a single-domain antibody consisting of the variable domain of one heavy chain, referred as variable domain of heavy chain of heavy-chain antibody (VHH). The VHH crystal, in a cylindrical shape, is of a diameter of 2.5 nanometers and a length of 4 nanometers, thus also known as nanobody (Nb) or single-domain heavy chain antibody.

The nanobody has been developed to be a highly versatile molecule having extensive values in both biological and clinical applications so far from discovery. The nanobody contains a minimal functional antigen-binding fragment derived from HCAbs in an adult camel, with high stability and high affinity when binding to an antigen, capable of interacting with an active site of protein cleaving enzyme so as to act in a manner similar to an inhibitor. Accordingly, the nanobody provides a novel way to design a small-molecule enzyme inhibitor from a peptidomimetic drug. It is easier to prepare a nanobody as compared to mAb due to the heavy chain contained only. Then, the nanobody, with particular characteristic (such as stability at extreme temperature and pH environment), can be prepared in a large scale with low costs. Therefore, the nanobody has great values in treatment and diagnosis of disease, particular in antibody targeting diagnosis and treatment against tumor.

Phage display technology, a traditional method for screening a camelid antibody, mainly includes: collecting a certain amount of peripheral blood or immunologic tissue from a camel after immunized; isolating lymphocytes; extracting mRNA; and inserting cDNA into a proper site of a structural gene of phage coat protein through PR-PCR, enabling an exogenous gene to express along expression of the coat protein, so as to form monoclone for antibody screening. However, the phase display technology, performed mostly on human, mouse, rabbit, seldom on camel, requires a relative long experimental period (approximately 77 days) and usually is used to screen a conventional antibody containing both the heavy chain and the light chain which are complementary to each other. It is evident that the phage display technology is not only time-consuming and labor-consuming, but also has great difficulties in technology.

As a result, the method for screening the nanobody still needs to be improved.

SUMMARY

The present disclosure seeks to solve at least one of the technical problems in the related art to some extent. Accordingly, the present disclosure provides in embodiments a method for screening mature nanobodies with high specificity, which may be accomplished in a short experimental period with high efficiency, but without analysis to random pairing of heavy and light chains.

In one aspect, the present disclosure provides in embodiments a method for screening a nanobody. In some embodiments, the method includes the following steps: (1) extracting a nucleic acid sample from tissue or peripheral blood obtained from an animal after immunized; (2) obtaining a sequencing result containing an antibody sequence based on the nucleic acid sample; (3) constructing an antibody database based on the sequencing result containing the antibody sequence; and (4) subjecting the antibody database to information analysis, to obtain sequence of nanobody.

In an embodiment of the present disclosure, the nanobody is obtained by screening with immune repertoireomics technology, i.e., polymerase chain reaction (PCR) or 5'-rapid amplification cDNA ends (5'-RACE technology), such that nanobody containing the heavy chain only, but no the light chain, are obtained rapidly and efficiently through direct screening. Such a screening method greatly shortens the experimental period for screening the nanobody (merely requiring about 21 days), thereby significantly enhancing screening efficiency. In addition, this screening method does not need to make analysis to random pairing of the heave and light chains, thereby effectively avoiding error analysis caused by mismatch between heavy and light chains. The nanobody thus obtained through screening has broad application prospects in various aspects such as disease diagnosis and treatment, drug development and food detection.

In an embodiment of the present disclosure, the method for screening the nanobody further includes the following steps: (5) subjecting serum obtained from the animal after immunized to protein mass spectrometry analysis to obtain a result of protein mass spectrometry; and (6) integrating information of the antibody database with the result of protein mass spectrometry for analysis to obtain sequence of the nanobody.

In an embodiment of the present disclosure, the method for screening the nanobody further includes: (7) expressing the nanobody via a protein expression system based on the sequence of the nanobody, to identify the nanobody.

In an embodiment of the present disclosure, the animal is a Camelidae family animal.

In an embodiment of the present disclosure, the Camelidae family animal is at least one selected from *Camelus dromedarius, Camelus bactrianus, Lama guanicoe, Lama glama, Vicugna vicugna*, and *Vicugna pacos*.

In an embodiment of the present disclosure, the antibody sequence includes a hypervariable region and a framework region.

In an embodiment of the present disclosure, the step (2) further includes the following sub-steps:

(2a) amplifying the antibody sequence in the nucleic acid sample to obtain an amplification product; and (2b) subjecting the amplification product to sequencing to obtain the sequencing result containing the antibody sequence.

In an embodiment of the present disclosure, the nucleic acid sample is DNA or RNA.

In an embodiment of the present disclosure, in the case that the nucleic acid sample is DNA, the antibody sequence in the nucleic acid sample is amplified by polymerase chain reaction (PCR); in the case that the nucleic acid sample is RNA, the antibody sequence in the nucleic acid sample is amplified by 5'-rapid amplification cDNA ends (5'-RACE) or polymerase chain reaction (PCR).

In an embodiment of the present disclosure, the PCR is at least one of multiplex PCR, linear amplification mediated PCR (LAM-PCR), and nested PCR.

In an embodiment of the present disclosure, the amplification product is sequenced on a high-throughput sequencing device.

In an embodiment of the present disclosure, the high-throughput sequencing device is at least one selected from a group consisting of llumina HiSeq2000, HiSeq2500k MiSeq, MiSeqDx, NextSeq500, Hiseq X ten, Life SOLiD, Ion Torrent PGM, Proton, Roche 454 and single molecule sequencing equipment. Thus, the sequencing has a high throughput and low cost.

In an embodiment of the present disclosure, the step (3) further includes the following sub-steps: (3a) aligning the sequencing result containing the antibody sequence to a reference sequence to determine an immune-related gene sequence; (3b) determining a nucleotide sequence of the antibody based on the immune-related gene sequence; (3c) translating the nucleotide sequence of the antibody into an amino acid sequence; and (3d) screening to obtain a VHH sequence based on the amino acid sequence, and constructing an antibody database.

In an embodiment of the present disclosure, the immune-related gene sequence is at least one selected from a V gene, a D gene, a J gene and a C gene.

In an embodiment of the present disclosure, the reference sequence is a known germline sequence in the absence of rearranging at least one of the V gene, the D gene, the J gene and the C gene.

In an embodiment of the present disclosure, in the sub-step (3d), an indicator of determining the amino acid sequence to be the VHH sequence includes at least one of:

A: a presence of any one of four conserved amino acids: 37F, 44E, 45R and 47G, in which 37F indicates that the amino acid at position 37 is phenylalanine (F); 44E indicates that the amino acid at position 44 is glutamate (E); 45R indicates that the acid at position 45 is arginine (R); 47G indicates that the acid at position 47 is glycine (G), whereas as to a common double-strand antibody, the amino acid at position 37 is valine (V), the amino acid at position 44 is glycine (G), the amino acid at position 45 is leucine (L), the amino acid at position 47 is tryptophan (W), where the first amino acid of the hypervariable region is at position 0, B: a presence of sequences shown as SEQ ID NO: 1 and SEQ ID NO: 2 in a hinge region, in which

```
                                              (SEQ ID NO: 1)
aacccaagataccccaaccacaaccaaaaccacaaccacaaccacaacca
caaccaaaaccacaaccaaaacctgaaccagaatgcacgtgtcccaaatg
tccag,
```

```
                                              (SEQ ID NO: 2)
ggaacgaatgaagtatgcaagtgtcccaaatgtcca,
```

C. absence of at least one portion of CH1; and

D. abnormal average length of CDR3, in which CDR3 is of a length varying in a wide range for both common antibody and VHH, however, CDR3 in the VHH sequence is of a longer average length than that of the common antibody.

In an embodiment of the present disclosure, the step (5) further includes: (5a) enriching IgG from the serum of the animal after immunized with Protein A/G to obtain an enriched product; (5b) affinity purifying, by a chromatographic column conjugated with the antigen, the antibody from the enriched product to obtain a purified product; (5c) subjecting the purified product to denaturation and reductive alkylation, and then lysing with protease to obtain an enzyme-digested peptide; and (5d) subjecting the enzyme-digested peptide to protein mass spectrometry analysis on mass spectrometer to obtain a mass spectrometry result of the enzyme-digested peptide.

In an embodiment of the present disclosure, the protease is at least one of pepsin, chymotrypsin, elastinase, trypsin, endoproteinase Lys-C, metalloendopeptidase Lys-N, endoproteinase Glu-C, aspartate endopeptidase Asp-N, and clostripain Arg-C.

In another aspect, the present disclosure provides in embodiments a system for screening a nanobody. In some embodiments, the system includes an extracting device configured to extract a nucleic acid sample from tissue or peripheral blood obtained from an animal after immunized by an antigen; a sequencing device configured to obtain a sequencing result containing an antibody sequence based on the nucleic acid sample; an antibody database constructing device configured to construct an antibody database based on the sequencing result containing the antibody sequence; and; an analysis device configured to subject the antibody database to information analysis, to obtain sequence of the nanobody.

In an embodiment of the present disclosure, the system further includes a protein mass spectrometry analysis device configured to subject serum obtained from the animal after immunized to protein mass spectrometry analysis to obtain a result of protein mass spectrometry; and an integrating and analyzing device configured to integrate information of the antibody database with the result of protein mass spectrometry for analysis to obtain the sequence of the nanobody.

In an embodiment of the present disclosure, the system further includes an identifying device configured to express the nanobody via a protein expression system based on the sequence of the nanobody, to identify the nanobody.

In an embodiment of the present disclosure, the animal is a Camelidae family animal.

In an embodiment of the present disclosure, the Camelidae family animal is at least one selected from *Camelus dromedarius, Camelus bactrianus, Lama guanicoe, Lama glama, Vicugna vicugna,* and *Vicugna* pacos.

In an embodiment of the present disclosure, the antibody sequence includes a hypervariable region and a framework region.

In an embodiment of the present disclosure, the sequencing device further includes: an amplifying unit configured to amplify the antibody sequence in the nucleic acid sample to obtain an amplification product; and a sequencing unit configured to subject the amplification product to sequencing to obtain the sequencing result containing the antibody sequence.

In an embodiment of the present disclosure, the nucleic acid sample is DNA or RNA.

In an embodiment of the present disclosure, in the case that the nucleic acid sample is DNA, the antibody sequence in the nucleic acid sample is amplified by PCR; in the case that the nucleic acid sample is RNA, the antibody sequence in the nucleic acid sample is amplified by 5'-RACE or PCR.

In an embodiment of the present disclosure, the PCR is at least one of multiplex PCR, linear amplification mediated PCR and nested PCR.

In an embodiment of the present disclosure, the sequencing unit is a high-throughput sequencing device.

In an embodiment of the present disclosure, the high-throughput sequencing device is at least one selected from a group consisting of llumina HiSeq2000, HiSeq2500k MiSeq, MiSeqDx, NextSeq500, Hiseq X ten, Life SOLiD, Ion Torrent PGM, Proton, Roche 454 and single molecule sequencing equipment.

In an embodiment of the present disclosure, the antibody database constructing device further includes: an aligning unit configured to align the sequencing result containing the antibody sequence to a reference sequence to determine an immune-related gene sequence; a determining unit configured to determine a nucleotide sequence of the antibody based on the immune-related gene sequence; a translating unit configured to translate the nucleotide sequence of the antibody into an amino acid sequence; a screening unit configured to screen to obtain a VHH sequence based on the amino acid sequence, and constructing the antibody database.

In an embodiment of the present disclosure, the immune-related gene sequence is at least one selected from a V gene, a D gene, a J gene and a C gene, In an embodiment of the present disclosure, the reference sequence is a known germline sequence in the absence of rearranging at least one of the V gene, the D gene, the J gene and the C gene.

In an embodiment of the present disclosure, an indicator of determining the amino acid sequence to be the VHH sequence by the screening unit comprises at least one of:

A: a presence of any one of four conserved amino acids: 37F, 44E, 45R and 47G,

B: a presence of sequences shown as SEQ ID NO: 1 and SEQ ID NO: 2 in a hinge region, C. absence of at least one portion of CH1; and D. abnormal average length of CDR3.

In an embodiment of the present disclosure, the protein mass spectrometry analysis device further includes: an enriching unit configured to enrich IgG from the serum of the animal after immunized with Protein A/G to obtain an enriched product; an affinity purifying unit configured to affinity purify, by a chromatographic column conjugated with the antigen, the antibody from the enriched product to obtain a purified product; a lysing unit configured to subject the purified product to denaturation and reductive alkylation, and then lysing with protease to obtain an enzyme-digested peptide; and a protein mass spectrometry measuring unit configured to subject the enzyme-digested peptide to protein mass spectrometry analysis on mass spectrometer to obtain a mass spectrometry result of the enzyme-digested peptide.

In an embodiment of the present disclosure, the protease is at least one of pepsin, chymotrypsin, elastinase, trypsin, endoproteinase Lys-C, metalloendopeptidase Lys-N, endoproteinase Glu-C, aspartate endopeptidase Asp-N, and clostripain Arg-C.

DETAILED DESCRIPTION

Figure 1:
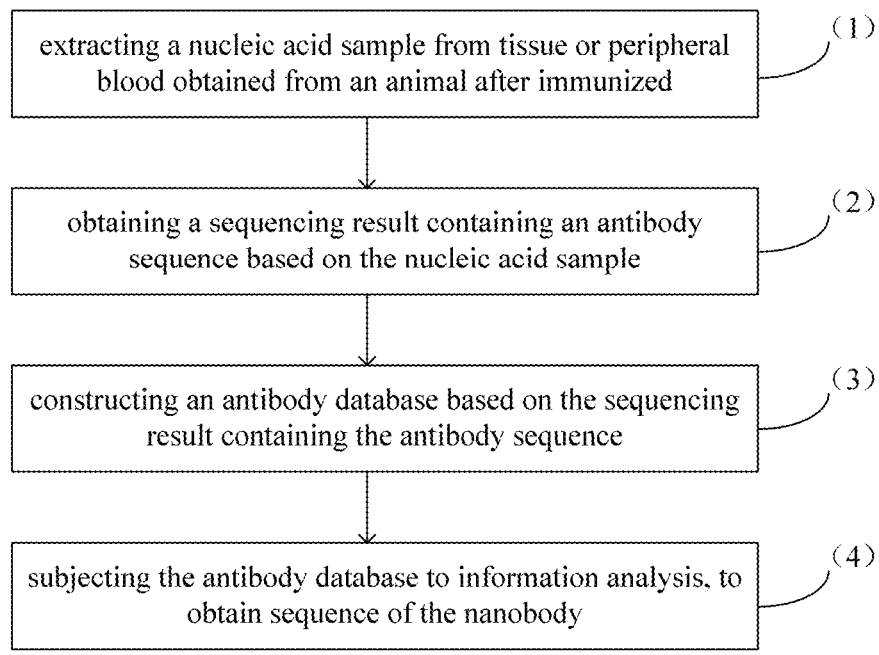
FIG. 1 is a flow chart showing a method for screening a nanobody in an embodiment of the present disclosure.

Reference will be made in detail to examples of the present disclosure. It would be appreciated by those skilled in the art that the following examples are explanatory, and cannot be construed to limit the scope of the present disclosure. If the specific technology or conditions are not specified in the examples, a step will be performed in accordance with the techniques or conditions described in the literature in the art or in accordance with the product instructions. If the manufacturers of reagents or instruments are not specified, the reagents or instruments may be commercially available.

In an aspect, the present disclosure provides in embodiments a method for screening a nanobody. In an embodiment of the present disclosure, the method includes the following steps (1) to (4).

(1) extracting a nucleic acid sample from tissue or peripheral blood obtained from an animal after immunized In an embodiment of the present disclosure, the animal with immunization is obtained by immunizing an animal with an antigen. In some embodiments of the present disclosure, the antigen used include, but not limited to cytokeratins 18 (CK18) in epithelial cells and nucleoside diphosphate kinase A (NDKA 863-17). In a specific embodiment of the present disclosure, the animal is immunized with the antigen at a dosage 10 mg each time.

In some embodiments of the present disclosure, the animal is a Camelidae family animal. In some embodiments of the present disclosure, the Camelidae family animal is at least one selected from *Camelus dromedarius*, *Camelus bactrianus*, *Lama guanicoe*, *Lama glama*, *Vicugna vicugna*, and *Vicugna pacos*. Therefore, efficiency of obtaining the nanobody is improved. In a specific embodiment, the animal is a camel.

(2) obtaining a sequencing result containing an antibody sequence based on the nucleic acid sample In an embodiment of the present disclosure, the step (2) further includes the following sub-steps (2a) and (2b).

(2a) amplifying the antibody sequence in the nucleic acid sample to obtain an amplification product In an embodiment of the present disclosure, the nucleic acid sample is DNA or RNA, thereby facilitating the subsequent step, and further improving the efficiency of obtaining the nanobody.

In an embodiment of the present disclosure, the antibody sequence includes a hypervariable region and a framework region, thereby effectively screening the nanobody.

In an embodiment of the present disclosure, in the case that the nucleic acid sample is DNA, the antibody sequence in the nucleic acid sample is amplified by polymerase chain reaction (PCR); in the case that the nucleic acid sample is RNA, the antibody sequence in the nucleic acid sample is amplified by 5'-rapid amplification cDNA ends (5'-RACE) or PCR. With the PCR or 5'-RACE technology, it only requires to design a specific primer for the C region, to effectively and comprehensively enrich the antibody sequence, such that expressing frequency rate of gene family; pairing of V and J genes; base insertion; base deletion; diversity of CDR and length distribution can be statistically calculated, and entire profile of whole antibody database against specific antigen can be observed, as well as the mature nanobody with high specificity can be cloned.

In an embodiment of the present disclosure, the PCR is at least one of multiplex PCR, linear amplification mediated PCR (LAM-PCR), and nested PCR.

(2b) subjecting the amplification product to sequencing to obtain the sequencing result containing the antibody sequence In an embodiment of the present disclosure, the amplification product is sequenced on a high-throughput sequencing device.

In another embodiment of the present disclosure, after library construction with the amplification product conventionally, a library for sequencing containing the amplification product obtained is sequenced on the high-throughput sequencing device.

In some embodiments of the present disclosure, the high-throughput sequencing device is at least one selected from a group consisting of llumina HiSeq2000, HiSeq2500k MiSeq, MiSeqDx, NextSeq500, Hiseq X ten, Life SOLiD, Ion Torrent PGM, Proton, Roche 454 and single molecule sequencing equipment, thereby rapidly and efficiently obtaining the nucleotide sequence of the nucleic acid sample with high sequencing through-put and low costs.

In some embodiment of the present disclosure, the sequencing result obtained in the sequencing step is filtered to remove reads with low quality as required.

(3) constructing an antibody database based on the sequencing result containing the antibody sequence In embodiments of the present disclosure, the step (3) further includes the following sub-steps (3a) to (3d).

(3a) aligning the sequencing result containing the antibody sequence to a reference sequence to determine an immune-related gene sequence In some embodiments of the present disclosure, the reference sequence is a known germline sequence in the absence of rearranging at least one of the V gene, the D gene, the J gene and the C gene, thereby rapidly and efficiently determining the immune-related gene sequence with high accuracy.

In some embodiments of the present disclosure, the immune-related gene sequence is at least one selected from a V gene, a D gene, a J gene and a C gene.

In some embodiments of the present disclosure, prior to aligning the sequencing result containing the antibody sequence to the reference sequence, the sequencing result containing the antibody sequence can be filtered as required, so as to remove reads with low quality and reads contaminated by adaptor, e.g. reads having low sequencing quality at terminal bases, reads having low average sequencing quality integrally or containing too much "N", reads contaminated by adaptor, and reads with too short length. In some embodiments of the present disclosure, in the case that the above high-throughput sequencing is performed based on paired-end (PE) sequencing, then PE reads after filtration are assembled based on overlap region.

In some embodiments of the present disclosure, the step of aligning the sequencing result containing the antibody sequence to the reference sequence specifically includes: aligning the sequencing result to the reference sequence using partial alignment software at first, and then aligning the sequencing result to the reference sequence again to obtain an aligning result. The reference sequence may be a known germline sequence of V/D/J/C genes in the absence of rearrangement. In some embodiments of the present disclosure, the partial alignment software includes but not limited to BLAST, BLASTN and LASTZ. Subsequently, corresponding sequences of V, D, J and C genes are determined respectively based on the alignment result. The heavy chain includes V, D, J and C genes. In the case that primers for both double strands of the common antibody sequence are designed and this double-strand antibody sequence is amplified, then the light chain of the double-strand antibody includes V, J and C genes.

(3b) determining a nucleotide sequence of the antibody based on the immune-related gene sequence It is known that both of the heavy and light chains include a complementarity determining region (CDR, also known as a hypervariable region) and a framework region. Accordingly, some parts of the sequence obtained, which can be aligned to the V and J genes of the germline sequence, can be determined, while the rest part of sequence obtained can be determined based on conserved regions.

In some embodiments of the present disclosure, after determined, the nucleotide sequence obtained is s subjected to various statistical analysis, including types of the CDR3 sequences, use distribution of the V gene, use distribution of the J gene, use distribution of paired V+J gene, length distribution of insertion or deletion in V, (D), J genes, base composition of the V gene, base composition of the J gene, frequency rate distribution of CDR3 sequence, and the like.

It should be noted that, expression "types of the CDR3 sequences" used herein refers to the number of different CDR3 sequences; expression "use distribution of the V gene" refers to frequency rate distribution of each type of the V gene used in all obtained sequences; expression "use distribution of the J gene" refers to frequency rate distribution of each type of the J gene used in all obtained sequences; expression "use distribution of paired V+J gene" refers to frequency rate distribution of each type of the paired V+J gene in all obtained sequences; expression "length distribution of insertion or deletion in the V, (D), or J gene" refers to length of inserted (usually between the genes) or deleted (usually at the ends of the gene) bases during V/D/J rearrangement; expression "base composition of the V gene" refers to base composition of the obtained sequences of each V gene at each reference sequence position and a proportion of each type of bases to all bases of the obtained sequences of each V gene; expression "base composition of the J gene" refers to base composition of the obtained sequences of each J gene at each reference sequence position and a proportion of each type of bases to all bases of the obtained sequences of each J gene; and expression "frequency rate distribution of CDR3" refers to the frequency rate distribution of each CDR3 to all obtained sequences.

(3c) translating the nucleotide sequence of the antibody into an amino acid sequence In some embodiments of the present disclosure, the amino acid sequence translated is subjected to the following statistical analysis, including abundance (indicating repeating times of one amino acid sequence), frequency rate (indicating a ratio of one amino acid sequence to all amino acid sequences), V and J genes corresponding to the amino acid sequence, and sequence information of the amino acid sequence. In this step, the amino acid sequence having abundance less than 2 is filtered out from the database.

(3d) screening to obtain a VHH sequence based on the amino acid sequence, and constructing the antibody database.

It should be noted that the VHH sequence obtained by screening in this step includes all VHH sequences obtained from the animal after immunized, i.e., both an immune antigen-related VHH sequence and an immune antigen-independent VHH.

In some embodiments of the present disclosure, an indicator of determining the amino acid sequence to be the VHH sequence includes at least one of:

A: a presence of any one of four conserved amino acids: 37F, 44E, 45R and 47G, in which 37F indicates that the amino acid at position 37 is phenylalanine (F); 44E indicates that the amino acid at position 44 is glutamate (E); 45R indicates that the acid at position 45 is arginine (R); 47G indicates that the acid at position 47 is glycine (G), whereas as to a common double-strand antibody, the amino acid at position 37 is valine (V), the amino acid at position 44 is glycine (G), the amino acid at position 45 is leucine (L), the amino acid at position 47 is tryptophan (W), where the first amino acid of the hypervariable region is at position 0, B: a presence of sequences shown as SEQ ID NO: 1 and SEQ ID NO: 2 in a hinge region, in which (SEQ ID NO: 1)
aacccaagatacccccaaccacaaccaaaaccacaaccacaaccacaacca
caaccaaaaccacaaccaaaacctgaaccagaatgcacgtgtcccaaatg
tccag, (SEQ ID NO: 2)
ggaacgaatgaagtatgcaagtgtcccaaatgtcca, C. absence of at least one portion of CH1; and D. abnormal average length of CDR3, in which CDR3 is of a length varying in a wide range for both common antibody and VHH, however, CDR3 in the VHH sequence is of a longer average length than that of the common antibody.

It should be further noted that in the case that primers for both double strands of the common antibody sequence are designed and this double-strand antibody sequence is amplified, the amino acid sequence obtained in step (3c) includes the nanobody and the double-strand antibody sequence, which can be separated by screening VHH antibody sequency, thereby obtaining both nanobody database and the double-strand antibody database. Those skilled in the art may choose the nanobody database directly for subsequent analysis to obtain the nanobody through screening, or choose both the nanobody database and the double-strand antibody database for subsequent analysis to obtain the nanobody through screening, thereby improving screening accuracy.

(4) subjecting the antibody database to information analysis, to obtain sequence of the nanobody In some embodiments of the present disclosure, the immune antigen-related nanobody sequence is obtained by screening based on frequency rate information in CDR3 of antibody.

Figure 2:
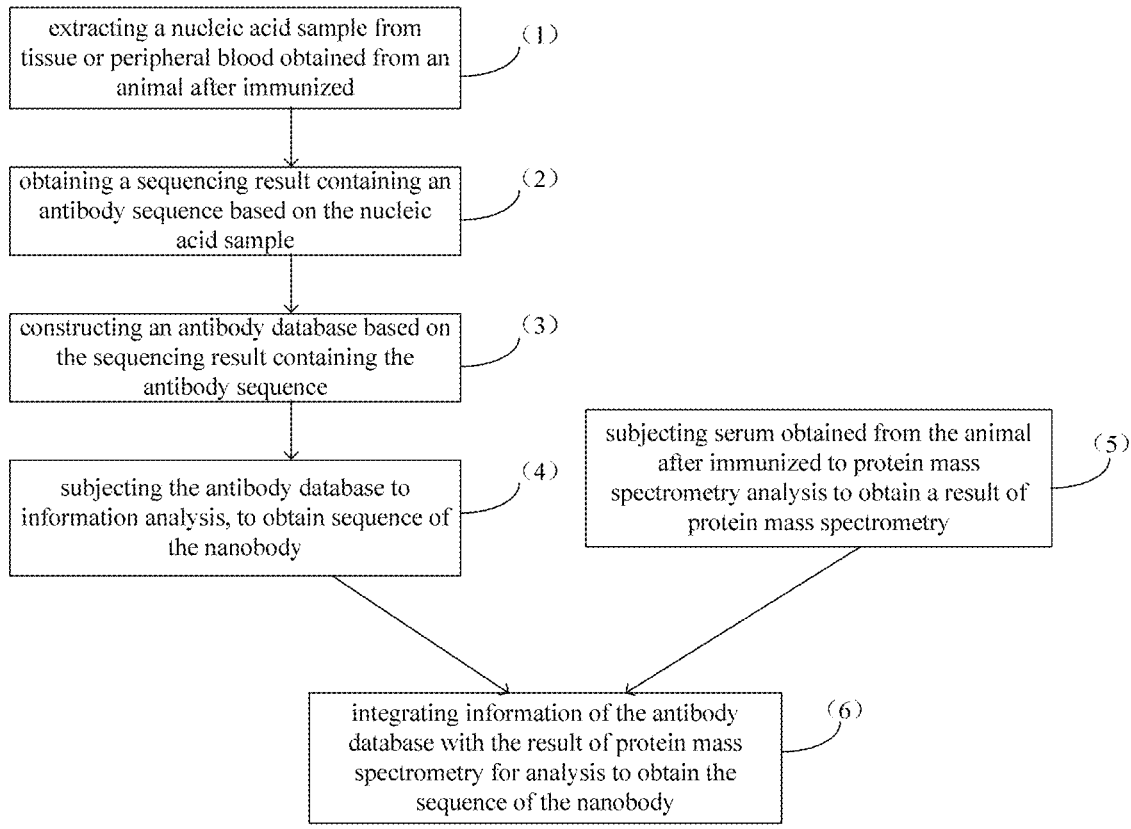
FIG. 2 is a flow chart showing a method for screening a nanobody in another embodiment of the present disclosure.
Figure 3:
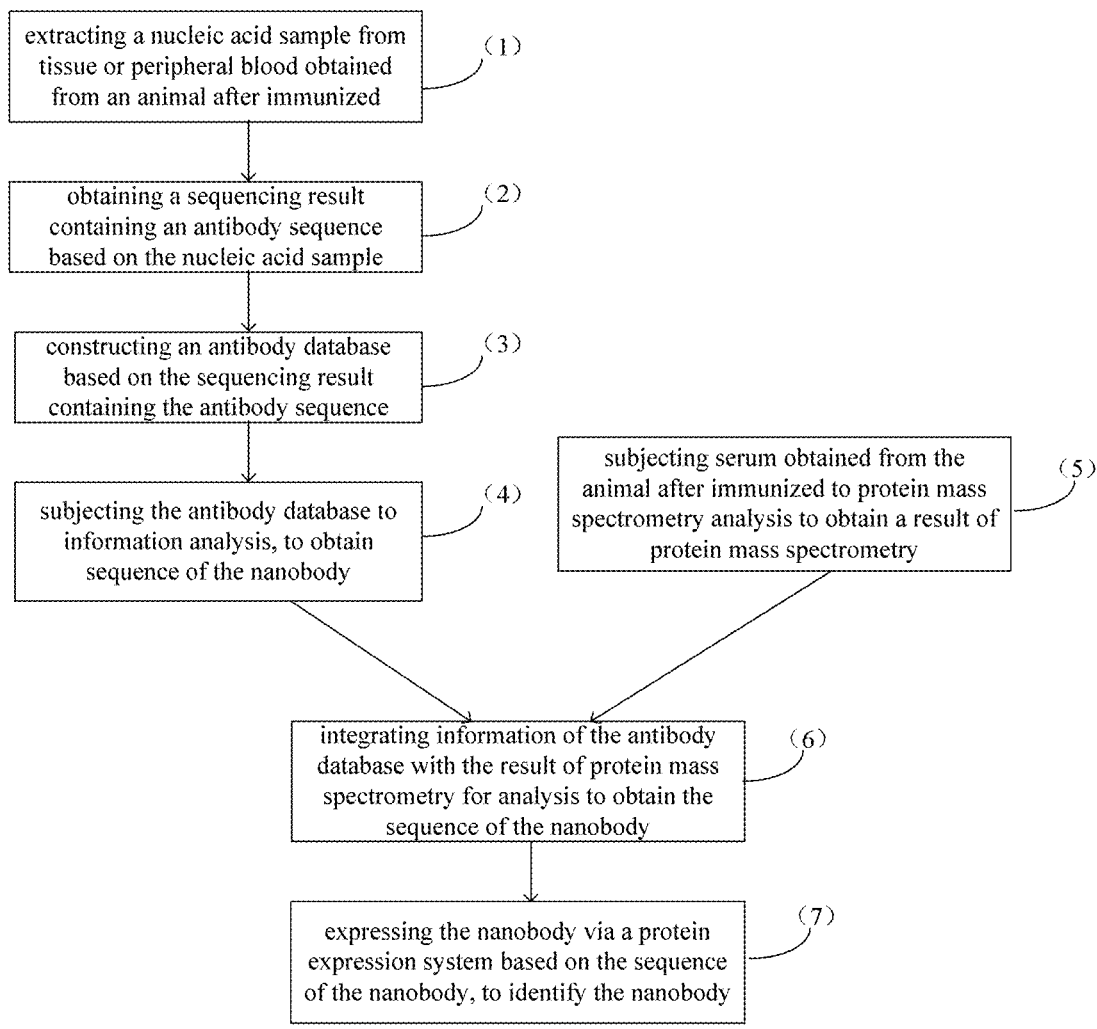
FIG. 3 is a flow chart showing a method for screening a nanobody in still another embodiment of the present disclosure.

In some embodiments of the present disclosure, the method for screening the nanobody further includes the following steps (5) and (6) as shown in FIG. 2.

(5) subjecting serum obtained from the animal after immunized to protein mass spectrometry analysis to obtain a result of protein mass spectrometry In some embodiments of the present disclosure, the step (5) further includes the following sub-steps (5a) to (5d).

(5a) enriching IgG from the serum of the animal after immunized with Protein A/G to obtain an enriched product In some embodiments of the present disclosure, after fatty acids, cell debris and granular substance are removed, IgG is enriched with Protein A/G from a serum sample obtained from the animal after immunized. The enriched product is detected by means of Western Blot or Enzyme Linked Immunosorbent assay (ELISA), to determine whether the enriched product thus obtained specifically binds to a known antigen polypeptide used.

(5b) affinity purifying, by a chromatographic column conjugated with the antigen, the antibody from the enriched product to obtain a purified product In some embodiments of the present disclosure, the enriched product obtained in step (5a) is affinity purified on a chromatographic column conjugated with antigen polypeptide used previously, thereby collecting flow-through and elution separately, both of which are subjected to Western Blot or ELASA, respectively, to determine whether affinity purified product specifically binds to the known antigen polypeptide used.

(5c) subjecting the purified product to denaturation and reductive alkylation, and then lysing with protease to obtain an enzyme-digested peptide In some embodiments of the present disclosure, the protease is at least one of pepsin, chymotrypsin, elastinase, trypsin, endoproteinase Lys-C, metalloendopeptidase Lys-N, endoproteinase Glu-C, aspartate endopeptidase Asp-N, and clostripain Arg-C.

(5d) subjecting the enzyme-digested peptide to protein mass spectrometry analysis on mass spectrometer to obtain a mass spectrometry result of the enzyme-digested peptide (6) integrating information of the antibody database with the result of protein mass spectrometry for analysis to obtain the sequence of the nanobody In some embodiments of the present disclosure, a common contamination protein sequence may be added into the antibody database at first, to obtain a final database. In some embodiments of the present disclosure, the contamination protein sequence includes: a sequence in the conserved region derived from species of the experimental subject, and a protein sequence derived from other species as interference.

In some embodiments of the present disclosure, the result of protein mass spectrometry can be compared with the antibody database by proper identification software with appropriate parameters, followed by a step of evaluating a false positive rate by means of Target-Decoy method, thereby retaining an identification result with low false positive rate (e.g. Below 1% or 5%) for subsequent analysis. Further, data obtained in protein mass spectrometry which is derived from different enzyme digestion may be merged together. Information such as the number of the identified peptides of the antibody sequence, protein coverage, and coverage of the identified peptides in the CDR3 was statistical calculated in accordance with corresponding relationship between the antibody and the identified peptide, followed by calculation of quantitative value of corresponding antibody sequence. Subsequently, combining frequency number information of the antibody sequence, the immune antigen-related nanobody sequence is obtained by screening based on a relationship among the number of identified peptide, the protein coverage and sequencing frequency rate of the antibody.

In a specific embodiment of the present disclosure, standards for screening include: the number of the identified peptides being not less than 20, the coverage of the identified peptides (obtained after merging data derived from different enzyme digestion) in the CDR3 being not less than 70%, the coverage of the identified peptides in whole V-region being not less than 50%, and frequency rate of Next-Generation Sequencing (NGS) being not under restriction.

In another specific embodiment of the present disclosure, standards for screening include: the number of the identified peptides being not less than 2, the coverage of the identified peptides (obtained after merging data derived from different enzyme digestion) being not under restriction, and frequency rate of Next-Generation Sequencing (NGS) being ranked in top 10.

In still another specific embodiment of the present disclosure, standards for screening include: the number of the identified peptides being not less than 20, the coverage of the identified peptides (obtained after merging data derived from different enzyme digestion) in the CDR3 being not less than 70%, the coverage of the identified peptides in whole V-region being not less than 35%, and frequency rate of Next-Generation Sequencing (NGS) being ranked in top 200.

In some embodiments of the present disclosure, the method for screening the nanobody further includes the following step (7) expressing the nanobody via a protein expression system based on the sequence of the nanobody, to identify the nanobody.

According to the technical solution of the present disclosure, the method for screening the nanobody can rapidly, effectively and directly obtain the nanobody containing the heavy chain only (without the light chain) through screening, which greatly shortens the experimental period for screening the nanobody (merely requiring about 21 days), thereby significantly enhancing screening efficiency. In addition, this screening method does not need to make analysis to random pairing of the heave and light chains, thereby effectively avoiding error analysis caused by mismatch between heavy and light chains.

Figure 8:
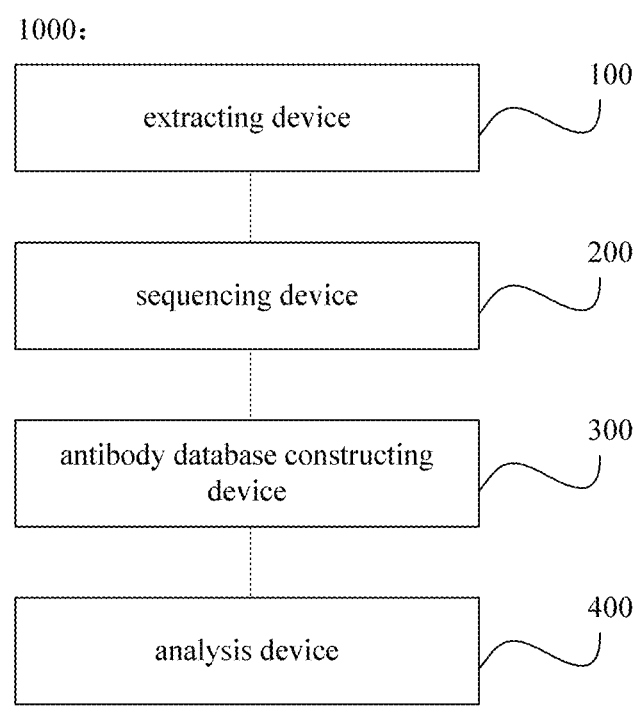
FIG. 8 is a schematic diagram showing a system for screening a nanobody in an embodiment of the present disclosure.
Figure 9:
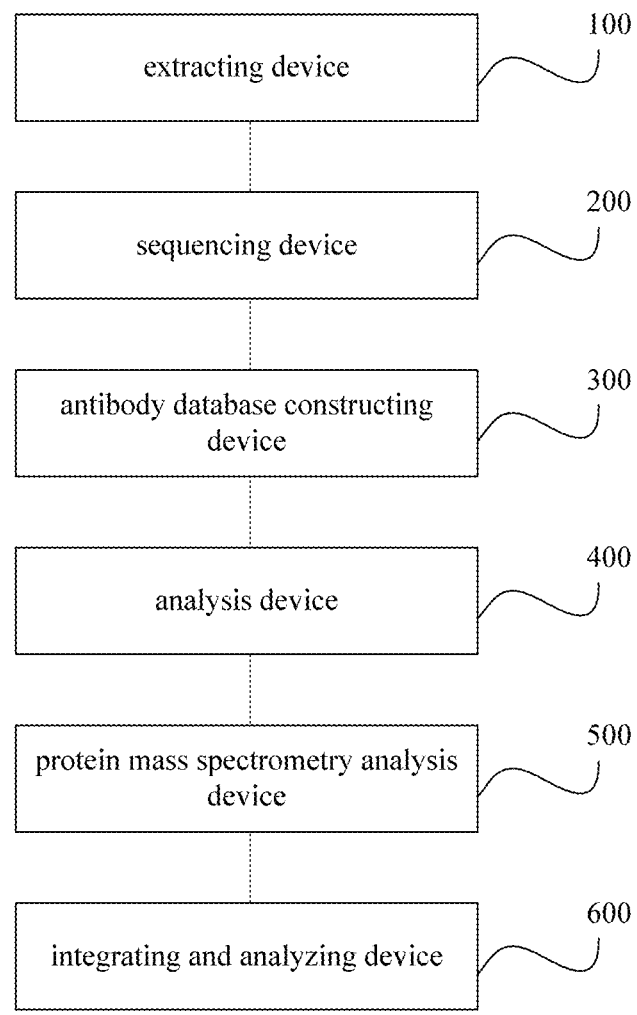
FIG. 9 is a schematic diagram showing a system for screening a nanobody in another embodiment of the present disclosure.
Figure 10:
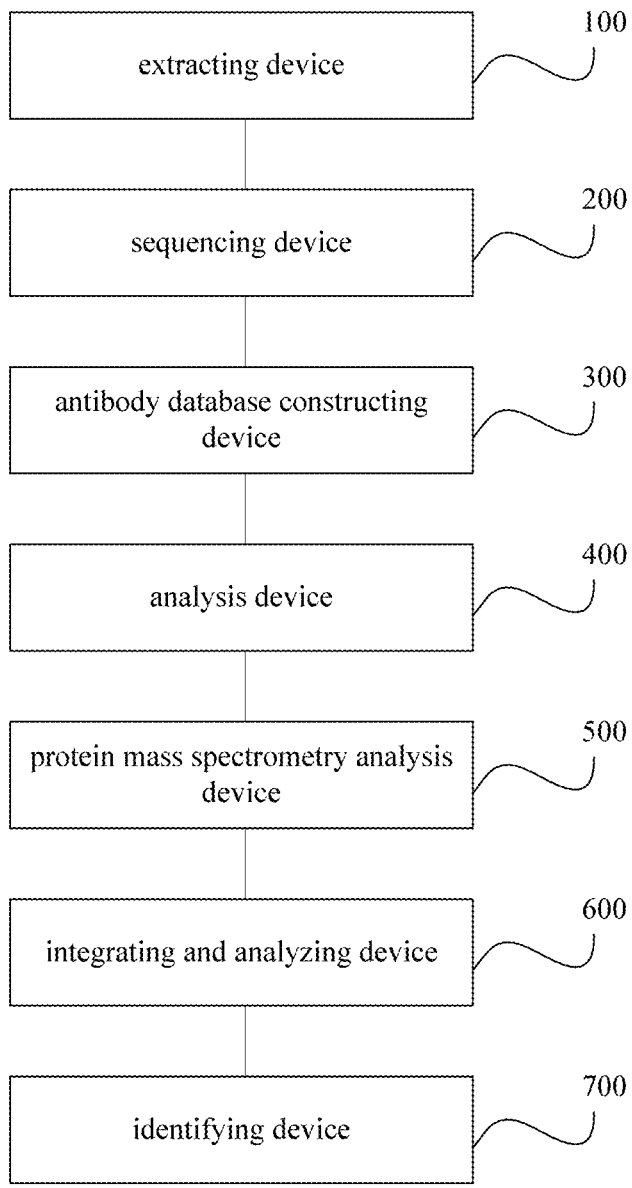
FIG. 10 is a schematic diagram showing a system for screening a nanobody in still another embodiment of the present disclosure.

In another aspect, the present disclosure provides a system 1000 for screening a nanobody. In an embodiment of the present disclosure, with reference to FIG. 8, the system includes an extracting device 100 configured to extract a nucleic acid sample from tissue or peripheral blood obtained from an animal after immunized by an antigen; a sequencing device 200 configured to obtain a sequencing result containing an antibody sequence based on the nucleic acid sample; an antibody database constructing device 300 configured to construct an antibody database based on the sequencing result containing the antibody sequence; and an analysis device 400 configured to subject the antibody database to information analysis, to obtain sequence of the nanobody.

In an embodiment of the present disclosure, the system 1000 further includes: a protein mass spectrometry analysis device 500 configured to subject serum obtained from the animal after immunized to protein mass spectrometry analysis to obtain a result of protein mass spectrometry; and an integrating and analyzing device 600 configured to integrate information of the antibody database with the result of protein mass spectrometry for analysis to obtain the sequence of the nanobody, In an embodiment of the present disclosure, the system 1000 further includes: an identifying device 700 configured to express the nanobody via a protein expression system based on the sequence of the nanobody, to identify the nanobody.

In an embodiment of the present disclosure, the animal is a Camelidae family animal.

In an embodiment of the present disclosure, the Camelidae family animal is at least one selected from *Camelus dromedarius, Camelus bactrianus, Lama guanicoe, Lama glama, Vicugna vicugna*, and *Vicugna* pacos.

In an embodiment of the present disclosure, the antibody sequence includes a hypervariable region and a framework region.

In an embodiment of the present disclosure, the sequencing device 200 further includes: an amplifying unit configured to amplify the antibody sequence in the nucleic acid sample to obtain an amplification product; and a sequencing unit configured to subject the amplification product to sequencing to obtain the sequencing result containing the antibody sequence.

In an embodiment of the present disclosure, the nucleic acid sample is DNA or RNA.

In an embodiment of the present disclosure, in the case that the nucleic acid sample is DNA, the antibody sequence in the nucleic acid sample is amplified by PCR; in the case that the nucleic acid sample is RNA, the antibody sequence in the nucleic acid sample is amplified by 5'-RACE or PCR.

In an embodiment of the present disclosure, the PCR is at least one of multiplex PCR, linear amplification mediated PCR and nested PCR.

In an embodiment of the present disclosure, the sequencing unit is a high-throughput sequencing device.

In an embodiment of the present disclosure, the high-throughput sequencing device is selected from a group consisting of llumina HiSeq2000, HiSeq2500k MiSeq, MiSeqDx, NextSeq500, Hiseq X ten, Life SOLiD, Ion Torrent PGM, Proton, Roche 454 and single molecule sequencing equipment, In an embodiment of the present disclosure, the antibody database constructing device 300 further includes: an aligning unit configured to align the sequencing result containing the antibody sequence to a reference sequence to determine an immune-related gene sequence; a determining unit configured to determine a nucleotide sequence of the antibody based on the immune-related gene sequence; a translating unit configured to translate the nucleotide sequence of the antibody into an amino acid sequence; a screening unit configured to screen to obtain a VHH sequence based on the amino acid sequence, and constructing the antibody database.

In an embodiment of the present disclosure, the immune-related gene sequence is at least one selected from a V gene, a D gene, a J gene and a C gene.

In an embodiment of the present disclosure, the reference sequence is a known germline sequence in the absence of rearranging at least one of the V gene, the D gene, the J gene and the C gene.

In an embodiment of the present disclosure, an indicator of determining the amino acid sequence to be the VHH sequence by the screening unit includes at least one of:

A: a presence of any one of four conserved amino acids: 37F, 44E, 45R and 47G, in which 37F indicates that the amino acid at position 37 is phenylalanine (F); 44E indicates that the amino acid at position 44 is glutamate (E); 45R indicates that the acid at position 45 is arginine (R); 47G indicates that the acid at position 47 is glycine (G), whereas as to a common double-strand antibody, the amino acid at position 37 is valine (V), the amino acid at position 44 is glycine (G), the amino acid at position 45 is leucine (L), the amino acid at position 47 is tryptophan (W), where the first amino acid of the hypervariable region is at position 0, B: a presence of sequences shown as SEQ ID NO: 1 and SEQ ID NO: 2 in a hinge region, in which

```
                                              (SEQ ID NO: 1)
acccaagataccccaaccacaaccaaaaccacaaccacaaccacaacca
caaccaaaaccacaaccaaaacctgaaccagaatgcacgtgtcccaaatg
tccag,
```

```
                                              (SEQ ID NO: 2)
ggaacgaatgaagtatgcaagtgtcccaaatgtcca,
```

C. absence of at least one portion of CH1; and

D. abnormal average length of CDR3, in which CDR3 is of a length varying in a wide range for both common antibody and VHH, however, CDR3 in the VHH sequence is of a longer average length than that of the common antibody.

In an embodiment of the present disclosure, the protein mass spectrometry analysis device 500 further includes: an enriching unit configured to enrich IgG from the serum of the animal after immunized with Protein A/G to obtain an enriched product; an affinity purifying unit configured to affinity purify, by a chromatographic column conjugated with the antigen, the antibody from the enriched product to obtain a purified product; a lysing unit configured to subject the purified product to denaturation and reductive alkylation, and then lysing with protease to obtain an enzyme-digested peptide; and a protein mass spectrometry measuring unit configured to subject the enzyme-digested peptide to protein mass spectrometry analysis on mass spectrometer to obtain a mass spectrometry result of the enzyme-digested peptide.

In an embodiment of the present disclosure, the protease is at least one of pepsin, chymotrypsin, elastinase, trypsin, endoproteinase Lys-C, metalloendopeptidase Lys-N, endoproteinase Glu-C, aspartate endopeptidase Asp-N, and clostripain Arg-C.

Example 1

Figure 6:
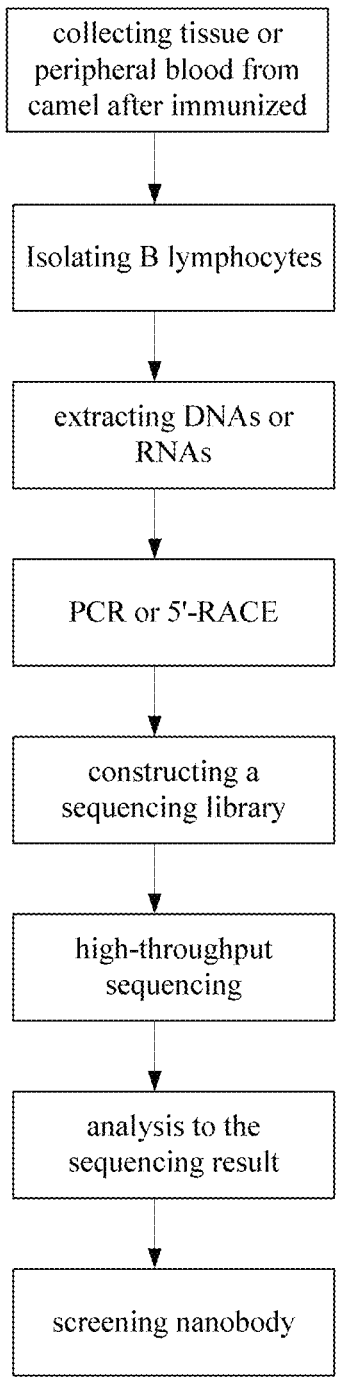
FIG. 6 is a flow chart showing a method for screening a nanobody by immune repertoireomics technology in an embodiment of the present disclosure.

Nanobody was obtained by screening with immune repertoireomics technology, as shown the flow chart in FIG. 6. In specific:

I. Designing a Primer for Enriching the Nanobody

Figure 4:
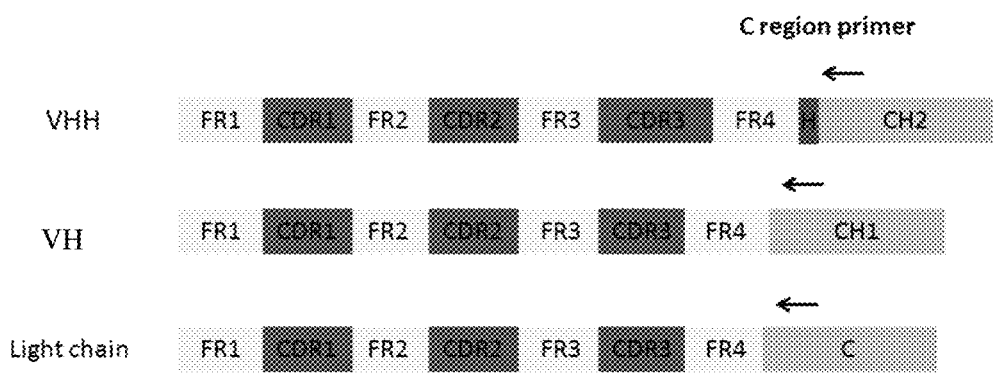
FIG. 4 is a schematic diagram showing primer design in an embodiment of the present disclosure.

A primer targeting a C domain was designed by taking an antibody of laboratory animal species (such as *Camelus dromedarius*, *Camelus bactrianus* and *Lama guanicoe*) in the IMGT database (www.imgt.org) as a reference sequence. FIG. 4 is a schematic view showing primer designs for VHH, a heavy chain of a common double-strand antibody (i.e., a common antibody) (i.e., a common VH), and a light chain of a normal double-strand antibody. Primer designs were conducted, targeting a CH2 domain for VHH; targeting a CH1 domain for the heavy chain of the common double-strand antibody; and targeting a C domain for the light chain of the normal double-strand antibody, respectively. In the present example, the primer designs were performed by Oligo6 software. Further, obtained primer sequences in primer designs were sent to and synthesized by a primer synthesis company. The primers have the sequence as shown below.

the primer targeting the CH2 domain in VHH:

```
                                              (SEQ ID NO: 3)
            5'-GGTACGTGCTGTTGAACTGTTCC-3';
``` the primer targeting the heavy chain of the common double-strand antibody:

```
                                              (SEQ ID NO: 4)
               5'-AGACCAGGCAGCCGAARG-3';
``` the primer targeting the light chain of the common double-strand antibody:

```
                                              (SEQ ID NO: 5)
              5'-GGAGTGGACTTGGGCTGAC-3';
```

```
                                              (SEQ ID NO: 6)
              5'-TGAGGGTGTAGCCTTGGGT-3';
```

```
                                              (SEQ ID NO: 7)
              5'-AARCACACGAYTGAGGCAC-3'.
```

II. Collecting Tissue or Peripheral Blood from an Animal after Immunized

The tissue sample (such as spleen, lymphonodus, intestinal tract and oral mucosa) and the peripheral blood sample were collected from camel after each of four immunizations with a known antigen polypeptide (such as CK18 and 863-17 (NDKA)) in an amount 1 mg per immunization and at an interval of every two weeks. From the tissue sample and the peripheral blood sample thus obtained, nucleic acid samples (DNA and RNA) were extracted for subsequent experiments.

III. Sequencing

With the primers mentioned above for enriching nanobodies, the DNA and RNA samples thus obtained were amplified by PCR; alternatively, the RNA sample thus obtained was amplified by 5'-rapid amplification cDNA ends (5'-RACE technology) or PCR, such that corresponding antibody sequence was obtained by amplification. In this amplification system, the nucleic acid sample was of an initial amount of 1 µg to 2 µg.

1. The RNA sample was amplified by the 5'-RACE technology, which had amplification system as shown below.

1.1 the following components were mixed at 37° C. for 10 min and held in an ice-bath for 1 min, thereby obtaining Solution A.

| each of the above primers | 2.5 pmol (10 to 25 ng) |
|---|---|
| RNA | 1-5 μg |
| DEPC-water | up to 15.5 μl |

1.2 The following components were added to the Solution A successively.

| 10 × PCR buffer | 2.5 μl |
|---|---|
| 25 mM MgCl$_2$ | 2.5 μl |
| 10 mM dNTP mixture | 1 μl |
| 0.1M DTT | 2.5 μl |

The total volume containing the above components was 24 which was spun down briefly and then incubated in an ice-bath for 1 min, thereby obtaining Solution B.

1.3 1 μl reverse transcriptase was added to the solution B, followed by mixed to be uniform and then reverse transcription in a warm-bath at a temperature of 42° C. for 50 min, thereby obtaining Solution C.

1.4 dCTP was added at the 5'-end

The following components were then added to the Solution C, thereby obtaining Solution D.

| DEPC-water | 6.5 μl |
|---|---|
| 5 × terminal deoxynucleotidyl transferase (TdT) buffer | 5.0 μl |
| 2 mM dCTP | 2.5 μl |
| S.N.A.P.-purified cDNA sample | 10.0 μl |
| total volume | 49.0 μl |

1.5 The Solution D was successively incubated at 94° C. for 2 to 3 min and in an ice-bath for 1 min followed by added with 1 μl terminal deoxynucleotidyl transferase (TdT), then after briefly centrifuge resulting solution was incubated at 65° C. for 10 min to inactivate TdT followed by placing on ice, thereby obtaining Solution E.

1.6 The Solution E was subjected to PCR amplification to enrich a targeting region, thereby obtaining Solution F.

| sterile distilled water | 31.5 μl |
|---|---|
| 10 × PCR buffer [200 mM Tris-HCl (pH 8.4), 500 mM KCl] | 5.0 μl |
| 25 mM MgCl$_2$ | 3.0 μl |
| 10 mM dNTP mixture | 1.0 μl |
| each of the above primers (10 μM) | 2.0 μl |
| anchor primer (10 μM) | 2.0 μl |
| dC-tailed cDNA | 5.0 μl |
| total volume | 49.5 μl | where the anchor primer has a sequence:

(SEQ ID NO. 8)
GGCCACGCGTCGACTAGTACGGGGGGGGGG.

After added with 0.5 μl Taq DNA polymerase, the solution F was subjected to firstly pre-denaturation at 94° C. for 2 min; then 35 cycles of PCR amplification, each cycle of which included denaturation at 94° C. for 0.5 min, annealing at 55° C. for 0.5 to 1 min, and extension for 72° C. for 1 min; and lastly final extension at 72° C. for 5 min.

2. The DNA sample was amplified by PCR, which had amplification system as shown below.

| 2 × KAPA pre-mixture | 25 μl |
|---|---|
| P1 primer (10 μM) | 1.5 μl |
| P2 primer (10 μM) | 1.5 μl |
| cDNA | 4.0 μl |
| DEPC-water | 18 μl | where the P1 primer and the P2 primer have sequences as shown below, respectively:

the P1 primer:
(SEQ ID NO. 9)
CTCTGCTCCTTCTCACCCTCCTCAC;

the P2 primer:
(SEQ ID NO. 10)
TCAGAGGACGGCGGGAACAGG.

Such a resulting solution containing the above components was subjected to firstly pre-denaturation at 94° C. for 3 min; then 35 cycles of PCR amplification, each of which included denaturation at 94° C. for 0.5 min, annealing at 55° C. for 0.5 min, and extension for 72° C. for 1 to 2 min; and lastly final extension at 72° C. for 5 min.

3. A library for sequencing was constructed for the antibody sequence thus obtained by amplification, in accordance with operating instructions provided by sequencer manufacturer.

For example, in the case that illumina Hiseq sequencing platform was used, the library for sequencing was constructed as the following step, according to the operating instructions.

3.1 end-repairing and adding base a at terminals

After gel-extraction and purification, resulting PCR amplification product was subjected to end-repairing with dNTPs as a substrate, T4 DNA Polymerase, Klenow Fragment, T4 Polynucleotide Kinase, and the like, thereby obtaining end-repaired terminal-phosphorylated DNA fragments. Such the end-repaired terminal-phosphorylated DNA fragments were then added base A at their 3' ends with Klenow Fragment (3'-5'exo-) polymerase and dATP. The resulting DNA sample was further collected from reaction system and purified by MiniElute PCR Purification Kit.

3.2 ligating an adaptor

The resulting DNA added with base A at 3' end was ligated with an adaptor by means of T4 DNA ligase, thereby obtaining a ligated product which was collected by Mini Elute PCR Purification Kit and quantified by Qubit method or the like.

3.3 cut-extracting and purifying the ligated product

The ligated product was collected by gel-cutting after agarose gel electrophoresis, and purified by Mini Elute PCR Purification Kit, thereby obtaining targeting DNA.

3.4 PCR amplification

The targeting DNA obtained was amplified as a template by PCR, together with a universal primer and Phusion high-fidelity DNA polymerase, thereby obtaining amplification product. After purifying with magnetic beads, the library for sequencing was obtained.

4. The library thus obtained was sequenced on at least one high-throughput sequencing platforms selected from Illumina HiSeq2000, HiSeq2500, MiSeq, MiSeqDx, NextSeq500, Hiseq X ten, Life SOLiD, Ion Torrent PGM, Proton, Roche 454 and single molecule sequencing, thereby obtaining a sequencing result. Filtration was then performed to remove reads with low quality as required.

IV. Analysis to the Sequencing Result

Figure 5:
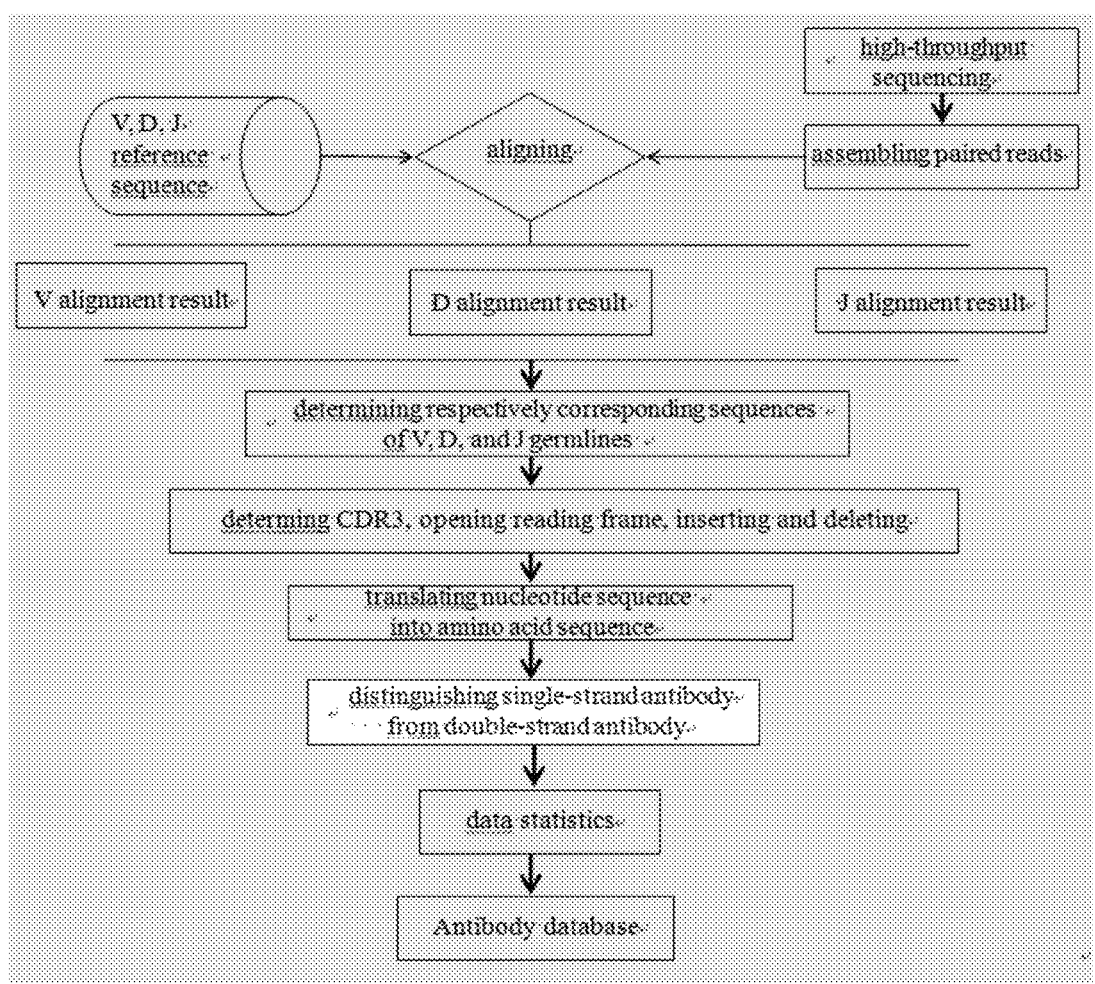
FIG. 5 is a flow chart showing steps of analyzing a sequencing result in an embodiment of the present disclosure.

A flow chart showing steps of analyzing the sequencing result was shown in FIG. 5.

1. The sequencing result was filtered base on the following standards:

1.1 removing reads contaminated by adaptor 1.2 removing reads having low sequencing quality at terminal bases 1.3 removing reads having low average sequencing quality integrally or containing too much After the above filtration, 62.87% to 75.67% reads were left behind from the sequencing result for common antibody library; while 55.14% to 71.64% reads were left behind for nanobody library, shown as Table 1 below.

2. In the case that the above high-throughput sequencing was perform based on paired-end (PE) sequencing, then PE reads after filtration were assembled based on overlap region.

Table 1 shows results of reads after preliminary process. As can be seen from Table 1, rates of successfully assembling PE reads for all samples are all above 91%.

TABLE 1

Result of Reads after Preliminary Process

| Sample | reads obtained in sequencing | reads left behind after removing adaptor-contaminated reads (%) | rate of successfully assembling PE reads (%) |
|---|---|---|---|
| 4-2-common antibody | 692821 | 63.94 | 92.86 |
| 4-4-common antibody | 585688 | 74.30 | 92.55 |
| 7- common antibody | 461284 | 73.69 | 92.94 |
| 10- common antibody | 540025 | 62.87 | 93.17 |
| 10-2- common antibody | 510276 | 68.16 | 92.59 |
| 10-4- common antibody | 544848 | 75.67 | 92.42 |
| 4-2-nanobody | 603930 | 56.86 | 92.13 |
| 4-4-nanobody | 610474 | 66.74 | 92.22 |
| 7-nanobody | 540738 | 64.22 | 92.15 |
| 10-nanobody | 525929 | 69.03 | 92.92 |
| 10-2-nanobody | 637110 | 55.14 | 92.47 |
| 10-4-nanobody | 573617 | 71.64 | 91.61 |

3. The sequence obtained after assemble was aligned to a reference sequence, which is a known germline sequence of V/D/J/C genes in the absence of rearrangement (www.imgt.org), using partial alignment software (such as BLAST, BLASTN and LASTZ). As bases may be deleted or inserted during V/D/J rearrangement, such the alignment was performed twice for more accurate determination on how many bases are deleted from or inserted into the sequence obtained as compared to the reference sequence. Corresponding sequences of V, D, J and C genes were determined respectively based on the alignment result. It is known that the heavy chain includes V, D, J and C genes; the light chain includes V, J and C genes; and both of them also include a complementarity determining region (CDR) and a framework region. Accordingly, some parts of the sequence obtained, which can be aligned to the V and J genes of the germline sequence, can be determined, while the rest part of sequence obtained can be determined based on conserved regions. Subsequently, the assembled nucleotide sequence was translated into an amino acid sequence. The V and J genes each have an aligning ratio as shown in Table 2, in which the V gene is of a relative low aligning ratio ranging from 45% to 71%, as a result of uncompleted reference sequence in the database; the J gene is of a relative high aligning ratio above 88%; and sequences which can be aligned to both of the V gene and the J gene are of an aligning ratio (V+J) ranging from 44% to 70%.

TABLE 2 aligning ratios for the V and J genes

| Sample | aligning ratio of the V gene (%) | aligning ratio of the J gene (%) | aligning ratio of the V + J gene (%) |
|---|---|---|---|
| 4-2-common antibody | 64.61 | 91.55 | 63.86 |
| 4-4-common antibody | 71.31 | 91.66 | 70.46 |
| 7-common antibody | 70.18 | 91.72 | 69.29 |
| 10-common antibody | 63.18 | 91.61 | 62.43 |
| 10-2-common antibody | 66.25 | 91.62 | 65.38 |
| 10-4-common antibody | 58.02 | 88.69 | 57.33 |
| 4-2-nanobody | 49.29 | 89.33 | 48.67 |
| 4-4-nanobody | 53.27 | 90.82 | 52.54 |
| 7-nanobody | 53.67 | 91.21 | 52.82 |
| 10-nanobody | 60.26 | 90.99 | 59.2 |
| 10-2-nanobody | 52.21 | 88.77 | 51.34 |
| 10-4-nanobody | 45.52 | 90.02 | 44.84 |

4. Screening a VHH sequence

The VHH sequence (including an immune antigen-related VHH gene and an immune antigen-independent sequence) was screened from the amino acid sequences obtained from translation in accordance with at least one of the following standards:

A: a presence of any one of four conserved amino acids: 37F, 44E, 45R and 47G, in which 37F indicates that the amino acid at position 37 is phenylalanine (F); 44E indicates that the amino acid at position 44 is glutamate (E); 45R indicates that the acid at position 45 is arginine (R); 47G indicates that the acid at position 47 is glycine (G), whereas as to a common double-strand antibody, the amino acid at position 37 is valine (V), the amino acid at position 44 is glycine (G), the amino acid at position 45 is leucine (L), the amino acid at position 47 is tryptophan (W), B: a presence of sequences shown as SEQ ID NO: 1 and SEQ ID NO: 2 in a hinge region, in which (SEQ ID NO: 1)
aacccaagatacccaaccacaaccaaaaccacaaccacaaccacaacca
caaccaaaaccacaaccaaaaacctgaaccagaatgcacgtgtcccaaatg
tccag, (SEQ ID NO: 2)
ggaacgaatgaagtatgcaagtgtcccaaatgtcca, C. absence of at least one portion of CH1; and D. abnormal average length of CDR3, in which CDR3 is of a length varying in a wide range for both common antibody and VHH, however, CDR3 in the VHH sequence is of a longer average length than that of the common antibody.

In the present example, it is preferred to screen the VHH sequence from the amino acid sequences meeting the above four standards at the same time.

Figure 11:
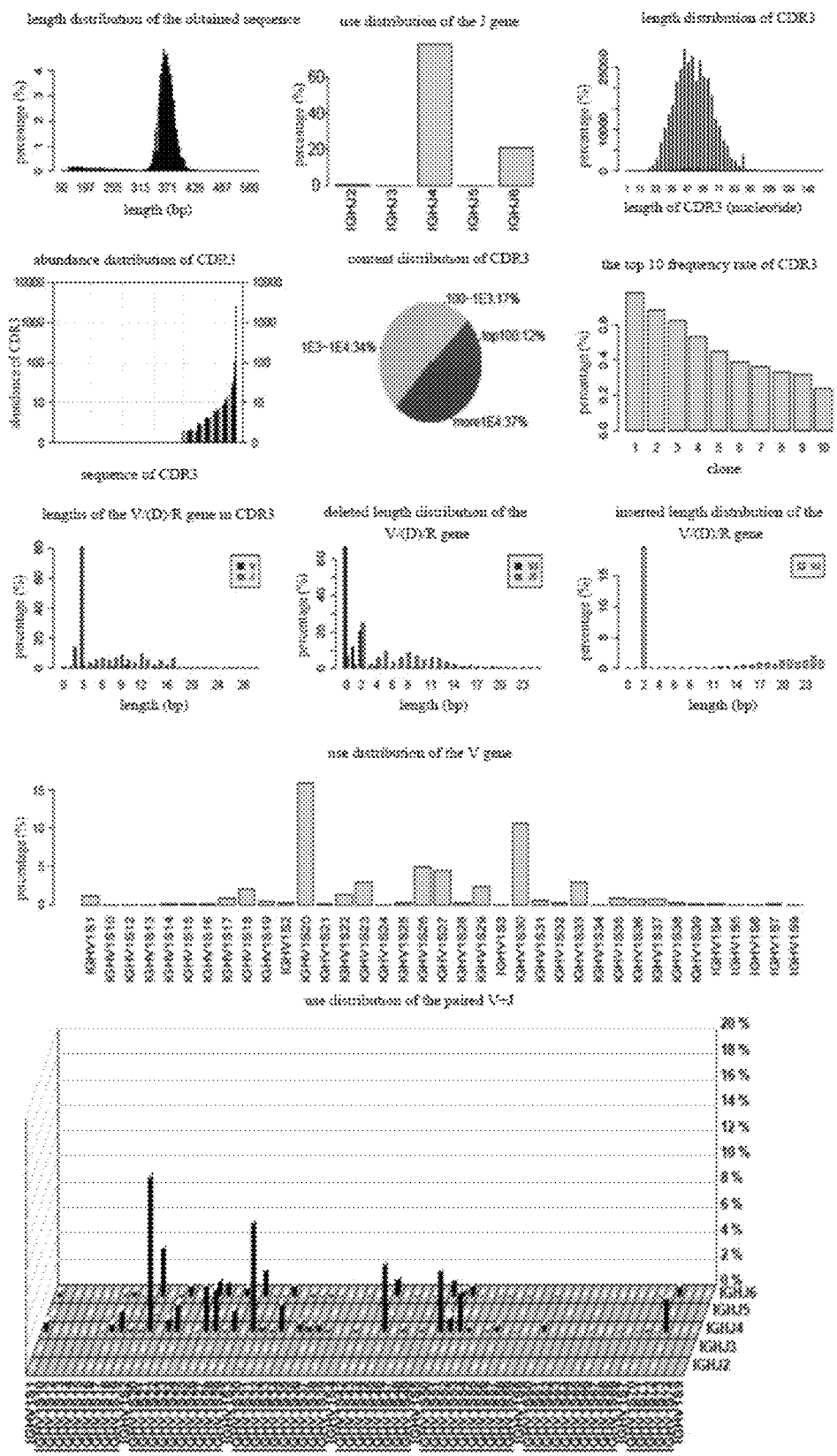
FIG. 11 includes diagrams showing statistic data analysis obtained from common Abs in an embodiment of the present disclosure.
Figure 12:
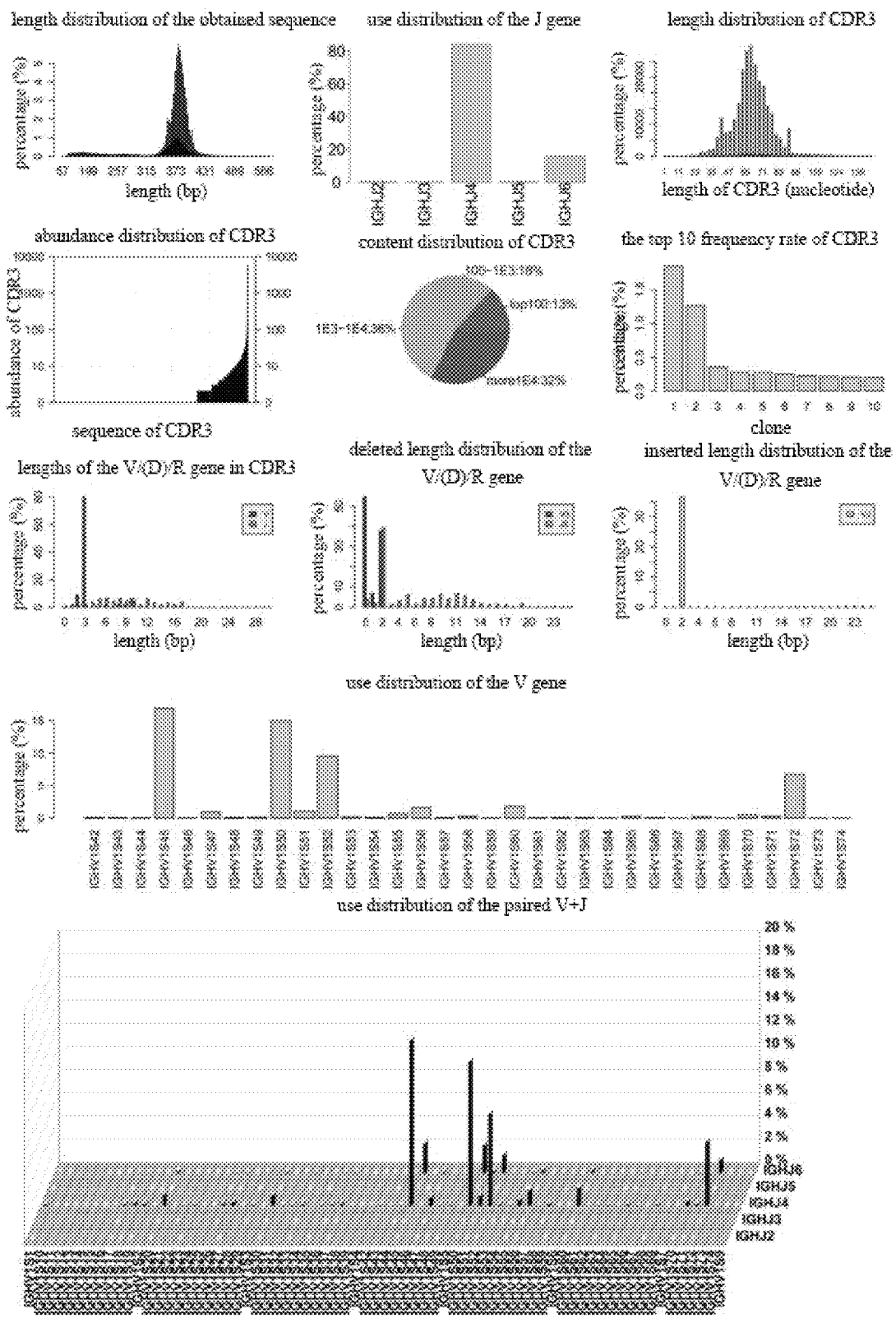
FIG. 12 includes diagrams showing statistic data analysis obtained from a nanobody in an embodiment of the present disclosure.
Figure 13:
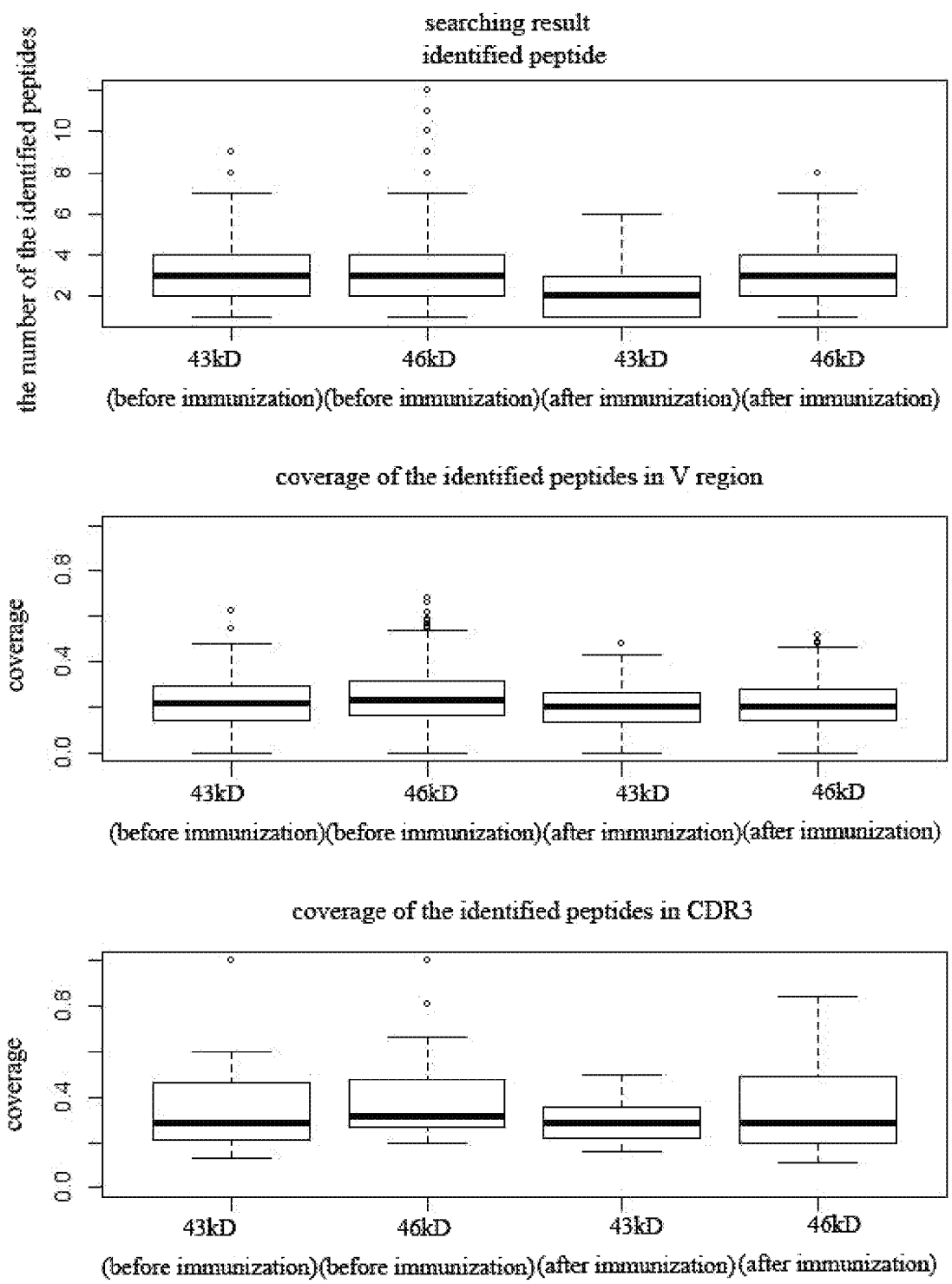
FIG. 13 includes diagrams showing statistical results of antibody peptide obtained, coverage of the antibody peptides obtained in the variable region, and coverage of the antibody peptides obtained in the CDR3 in an embodiment of the present disclosure.

5. The nucleotide sequence assembled in step 3 was subjected to various statistical analysis, including types of the CDR3 sequences, use distribution of the V gene, use distribution of the J gene, use distribution of paired V+J gene, length distribution of inserted or deleted in V, (D), J genes, base composition of the V gene, base composition of the J gene, frequency rate distribution of CDR3 sequence, and the like. Specific statistical results are shown in FIG. 11 (common antibody) and FIG. 12 (nanobody).

6. The amino acid sequence translated in step 3 was subjected to the following statistical analysis, including abundance (indicating repeating times of one amino acid sequence), frequency rate (indicating a ratio of one amino acid sequence to all amino acid sequences), V and J genes corresponding to the amino acid sequence, and sequence information of the amino acid sequence. These statistical results were used for constructing antibody database, including double-strand antibody database and single-strand antibody database. The amino acid sequence having abundance less than 2 was filtered out from the database in this step. Part of the antibody database constructed was shown in Table 3.

TABLE 3

Part of the antibody database

| Clones (amino acids) | sequence abundance | sequence frequency rate |
|---|---|---|
| MAHVQLVESGGGAVQTGGSLRLTCTAVGLTFEGGNQGWYR ETPGNEFELVSSIAPDGSRWYADSVQGRFTISRNVLPERLSL QMTRLKAEDTAMYYCAAGPDVGREKHLTADQVLSIRRNNF WGQGTQVTVS (SEQ ID NO: 11) | 112 | 0.037424 |
| MAHVQLVESGGGSVQTGGSLRLSCKPSFFILDDFDMMWYR QAPGNECELVSSISGDGSTYYTDAVKGRFTISHDNAKNSVD LQMNSLKPDDTAVYYCAATGQMLSVAGCRTQGTQVTVS (SEQ ID NO: 12) | 108 | 0.036087 |
| MADVQLVESGGGSVQTGGSLRLSCKPSFFILDDFDMMWYR QAPGNECELVSSISGDGSTYYTDAVKGRFTISHDNAKNSVD LQMNSLKPDDTAVYYCAATGQMLSVAGCRTQGTQVTVS (SEQ ID NO: 13) | 48 | 0.016039 |
| MAHVQLVESGGGSVQAGGSLSLSCATRGYTRRSGCLAWFR QVPGKEREMVAQIQDDGAKHYDSTAEGRFTISKDAAKDTL DLRMTSLKPEDSGMYYCAVDGPVAFCSDYPSDFRGWGQGT QVTVS (SEQ ID NO: 14) | 44 | 0.014702 |
| MADVQLVESGGGAVQTGGSLRLTCTAVGLTFEGGNQGWYR ETPGNEFELVSSIAPDGSRWYADSVQGRFTISRNVLPERLSL QMTRLKAEDTAMYYCAAGPDVGREKHLTADQVLSIRRNNF WGQGTQVTVS (SEQ ID NO: 15) | 40 | 0.013366 |
| VKGRFTISHDNAKNSVDLQMNSLKPDDTAVYYCAATGQML SVAGCRTQGTQVTVS (SEQ ID NO: 16) | 30 | 0.010024 |
| MAHVQLVESGGGEVQAGGSLKLSCAGSAYILENCGMVWY RQTKGKEEKLVSVRKDGTPVYEDTVKGRFTLSHDRSKNTM YLQMDNLKTEDTGVYYCAALNSTYGGRFGWCKDFRGQG TQVTVS (SEQ ID NO: 17) | 29 | 0.00969 |
| MAHVQLVESGGGSVQAGGSLKLTCAGSAYILEQCGMGWF RQAPGKEENLVSLRRDGTTVYSDSVKGRFTISQDRTKNILYL QMNDLKDEDTGMYYCAALNSSSGGRFAWCSDFRGQGTQV TVS (SEQ ID NO: 18) | 28 | 0.009356 |
| MAHVQLVESGGGSVQAGGSLRLSCAISGRSNENYFLAWFR QPPGKEREGVAAMYTGFGGGNIYYDDSVKGRFTISQDNSK NTLFLQMNVLRPEDTAMYYCAARKVARGSHFSLGRAPALR RDEYNFWGQGTQVTVS (SEQ ID NO: 19) | 25 | 0.008354 |
| MAHVQLVESGGGSVQAGGSLRLSCTHSGYISSRHCMGWFR QAPGKAREGIAGIRRDGDEYYAGSVKGRFTISQDNAKNIIY LQMSSLTPDDTAMYYCAAGTRIIVGDYCDGITTWGQGTQV TVS (SEQ ID NO: 20) | 25 | 0.008354 |

7. The immune antigen-related nanobody was then screened out according to the abundance of CDR3 of antibody. Specific screening standard is not less than 5, and preferably antibody sequence having a high abundance of CDR3 is preferred.

Example 2

Figure 7:
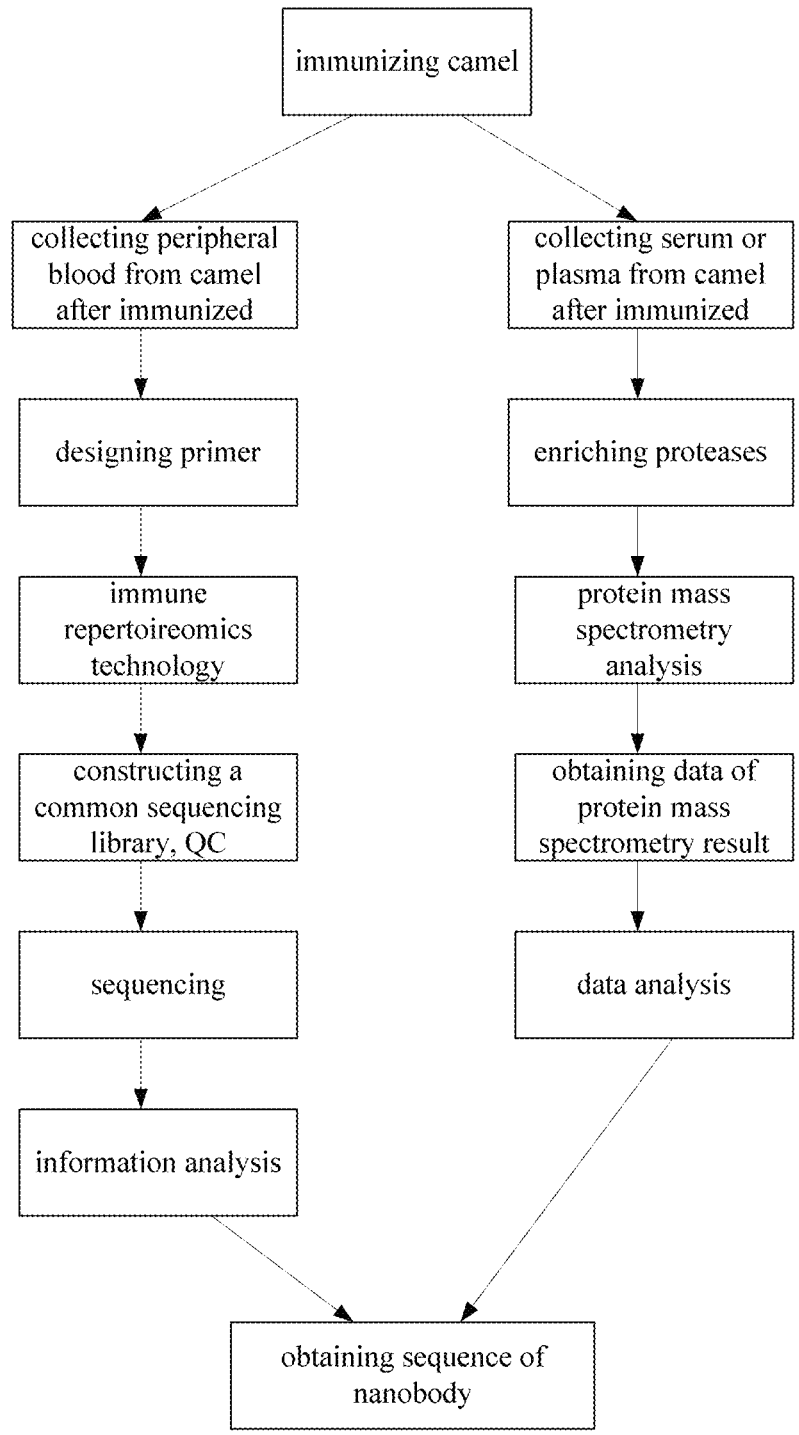
FIG. 7 is a flow chart showing a method for screening nanobody by combining immune repertoireomics technology with protein mass spectrometry analysis in an embodiment of the present disclosure.

In the present example, the nanobody was screened by further combining protein mass spectrometry on the basis of Example 1. The method for screening nanobody by combining immune repertoireomics technology with protein mass spectrometry was illustrated in a flow chart as shown in FIG. 7.

I. Experimental Protocol of Protein Mass Spectrometry 1. affinity purification of antibody 1.1 IgG enrichment After fatty acids, cell debris and granular substance were removed, IgG was enriched with Protein A/G from a serum sample obtained from a camel after immunized with an antigen (such as CK18 and 863-17 (NDKA)), thereby obtaining an enriched product. Subsequently, it was determined whether the enriched product thus obtained specifically binds to a known antigen polypeptide used, by means of Western Blot or Enzyme Linked Immunosorbent assay (ELISA).

1.2 affinity purification

The enriched product was affinity purified on a chromatographic column conjugated with antigen polypeptide used in Example 1, thereby collecting flow-through and elution separately, both of which were subjected to Western Blotting or ELASA, respectively, to determine whether affinity purified product specifically binds to the known antigen polypeptide used.

2. enzyme-digesting the affinity purified antibody and mass spectrometric detection After denaturation and reductive alkylation, aliquots of enriched antibody were enzyme digested with different proteases such as pepsin, chymotrypsin, elastinase, trypsin, endoproteinase Lys-C, metalloendopeptidase Lys-N, endoproteinase Glu-C, aspartate endopeptidase Asp-N, and clostripain Arg-C, respectively, thereby obtaining enzyme-digested peptides, which were then subjected to mass spectrometric detection for protein mass spectrometric result.

II. Analysis Method of Protein Mass Spectrometric Information 1. database construction The database including the antibody obtained by sequencing and analysis in Example 1 was incorporated with a common contamination protein sequence, thereby obtaining a final database. The contamination protein sequence used herein includes: a sequence in the conserved region derived from species of the experimental subject, and a protein sequence derived from other species as interference. The composition of the final database is shown as in Table 4 below.

TABLE 4

The final database and the number of sequences it contains

| Data source | the number of sequences |
| --- | --- |
| Reads derived from the heavy chain of the common antibody obtained from #4 camel after the second immunization (frequency rate is greater than 1) | 1732 |
| Reads derived from the nanobody obtained from #4 camel after second immunization (frequency rate is greater than 1) | 1479 |
| Reads derived from the heavy chain of the common antibody obtained from #4 camel after fourth immunization (frequency rate is greater than 1) | 1424 |
| Reads derived from the nanobody obtained from #4 camel after fourth immunization (frequency rate is greater than 1) | 2246 |
| Reads derived from the heavy chain of the common antibody obtained from #10 camel after second immunization (frequency rate is greater than 1) | 989 |
| Reads derived from the nanobody obtained from #10 camel after second immunization (frequency rate is greater than 1) | 1360 |
| Reads derived from the heavy chain of the common antibody obtained from #10 camel after fourth immunization (frequency rate is greater than 1) | 1580 |
| Reads derived from the nanobody obtained from #10 camel after second immunization (frequency rate is greater than 1) | 3104 |
| Reads derived from the heavy chain of the common antibody obtained from #10 camel (frequency rate is greater than 1) | 876 |
| Reads derived from the nanobody obtained from #10 camel immunization (frequency rate is greater than 1) | 1697 |
| Reads derived from the heavy chain of the common antibody obtained from #7 camel (frequency rate is greater than 1) | 601 |
| Reads derived from the nanobody obtained from #7 camel immunization (frequency rate is greater than 1) | 1132 |
| Common contamination protein | 115 |
| Yeast protein | 6718 |
| Total | 25053 |

2. Database Identification

The protein mass spectrometric result was identified by Mascot (www.matrixscience.com), and filtered by Mascot Percolator (www.sanger.ac.uk/resources/software/mascot-percolator/). Most parameters used for software are shown as below.

| | |
| --- | --- |
| Search engine | Mascot Percolator |
| Enzyme digestion | trypsin/chymotrypsin |
| Fixed modification | Cysteine-Carbamidomethyl i.e., Carbamidomethyl (C) |
| Differential modification | Methionine-Oxidation, (i.e., Oxidation (M)), deamidate (NQ) |
| Maximal missed cleavages | 1 |
| Mass tolerance for the parent ions | 20 ppm |
| Mass tolerance for fragment ions | 0.05 Da |
| Cut-off of false positive rate | 1% of peptide level |
| Standard for inferring protein | Each identified protein is required to have one or more unique peptides |

3. False positive rate control and identified peptide screening

The false positive rate of the identification result obtained in the above step was evaluated by Target-Decoy method. The identification result with low false positive rate was used for subsequent analysis, assuming that cut-off of the false positive rate is 1%.

4. Statistical analysis of coverage and abundance, as well as correlation analysis After data derived from different enzyme digestion was merged together, information such as the number of the identified peptides of the antibody sequence, coverage of the identified peptides in the variable region, and coverage of the identified peptides in the CDR3 was statistical calculated in accordance with corresponding relationship between the antibody and the identified peptide, followed by calculation of quantitative value of corresponding antibody sequence. Coverage indicates a proportion of lengths covered of all identified peptides to the total lengths of all identified peptides. The number of identified peptides indicates the number of all identified peptides having a false positive rate higher than the cut-off of the false positive rate. Statistical results of the antibody peptides obtained, the coverage of the identified peptides in the variable region, and coverage of the identified peptides in the CDR3 are shown in Table 13.

Combining the frequency number of antibody sequence, a relationship among the number of the identified peptides, the protein coverage and sequencing frequency rate of the antibody was analyzed, based on which the immune antigen-related nanobody sequence was obtained by screening.

In specific, standards for screening is any one the followings:

(1) the number of the identified peptides being not less than 6, the coverage of the identified peptides (obtained after merging data derived from different enzyme digestion) in the CDR3 being not less than 50%, the coverage of the identified peptides in whole V-region being not less than 40%, and frequency rate of Next-Generation Sequencing (NGS) being not under restriction;

(2) the number of the identified peptides being not less than 2, the coverage of the identified peptides (obtained after merging data derived from different enzyme digestion) being not under restriction, and frequency rate of Next-Generation Sequencing (NGS) being ranked in top 10; and (3) the number of the identified peptides being not less than 4, the coverage of the identified peptides (obtained after merging data derived from different enzyme digestion) in the CDR3 being not less than 50%, the coverage of the identified peptides in whole V-region being not less than 35%, and frequency rate of Next-Generation Sequencing (NGS) being ranked in top 200.

The following sequences were obtained and separated according to the above screening standards:

(1) the number of the identified peptides being not less than 6, the coverage of the identified peptides (obtained after merging data derived from different enzyme digestion) in the CDR3 being not less than 50%, the coverage of the identified peptides in whole V-region being not less than 40%, and frequency rate of Next-Generation Sequencing (NGS) being not under restriction:

| antibody name | the number of the identified peptides (before immunization) | coverage of the identified peptides in the variable region (before immunization) | coverage of the identified peptides in the CDR3 (before immunization) | antibody type | the number of the identified peptides (after immunization) | coverage of the identified peptides in the variable region (after immunization) | coverage of the identified peptides in the CDR3 (after immunization) |
|---|---|---|---|---|---|---|---|
| C10WBA-IgG23_26 | 9 | 0.624 | 0.5 | VHH | 5 | 0.48 | 0.5 |
| C10WBA-IgG23_1064 | 12 | 0.588652482269504 | 0.805555555555556 | VHH | 6 | 0.48936170212766 | 0.666666666666667 |
| C10WBA-IgG23_666 | 8 | 0.619402985074627 | 0.607142857142857 | VHH | 4 | 0.358208955223881 | 0 |

(2) the number of the identified peptides being not less than 2, the coverage of the identified peptides (obtained after merging data derived from different enzyme digestion) being not under restriction, and frequency rate of Next-Generation Sequencing (NGS) being ranked in top 10:

| antibody name | the number of the identified peptides (before immunization) | coverage of the identified peptides in the variable region (before immunization) | coverage of the identified peptides in the CDR3 (before immunization) | antibody type | the number of the identified peptides (after immunization) | coverage of the identified peptides in the variable region (after immunization) | coverage of the identified peptides in the CDR3 (after immunization) | rank of frequencies |
|---|---|---|---|---|---|---|---|---|
| C10WBA-IgG23_26 | 9 | 0.624 | 0.5 | VHH | 5 | 0.48 | 0.5 | 26 |
| C10WBA-IgG23_89 | 4 | 0.305785123966942 | 0 | VHH | 3 | 0.305785123966942 | 0 | 89 |
| C7WBA-IgG1_26 | 4 | 0.388888888888889 | 0 | VHH | 3 | 0.259259259259259 | 0 | 26 |
| C10-2-VHH-IgG1_90 | 3 | 0.16260162601626 | 0 | VH | 3 | 0.16260162601626 | 0 | 90 |
| C10WBA-IgG23_26 | 8 | 0.68 | 0.5 | VHH | 5 | 0.464 | 0.5 | 26 |
| C10WBA-IgG23_81 | 7 | 0.338842975206612 | 0 | VHH | 5 | 0.322314049586777 | 0 | 81 |
| C4-2-VHH-IgG23_61 | 3 | 0.23015873015873 | 0 | NA | 2 | 0.126984126984127 | 0 | 61 |
| C4-4-VHH-IgG23_84 | 2 | 0.169491525423729 | 0 | NA | 2 | 0.169491525423729 | 0 | 84 |
| C7WBA-IgG1_45 | 3 | 0.23728813559322 | 0 | NA | 4 | 0.271186440677966 | 0 | 45 |
| C7WBA-2 IgG23_82 | 2 | 0.155038759689922 | 0 | VHH | 2 | 0.155038759689922 | 0 | 82 |

(3) the number of the identified peptides being not less than 4, the coverage of the identified peptides (obtained after merging data derived from different enzyme digestion) in the CDR3 being not less than 50%, the coverage of the identified peptides in whole V-region being not less than 35%, and frequency rate of Next-Generation Sequencing (NGS) being ranked in top 200:

2.2.5 The third mixture was incubated at 37° C. for 45 min, thereby obtaining a fourth mixture.

2.2.6 After centrifuged at 5000 rpm for 3 mM, most supernatant of the fourth mixture was discarded, with about 100 µl to 150 µl residues left behind. Such the residues was resuspended in LB medium and then spread onto an LB/kanamycin agar plates.

| antibody name | the number of the identified peptides (before immunization) | coverage of the identified peptides in the variable region (before immunization) | coverage of the identified peptides in the CDR3 (before immunization) | antibody type | the number of the identified peptides (after immunization) | coverage of the identified peptides in the variable region (after immunization) | coverage of the identified peptides in the CDR3 (after immunization) | rank of frequencies |
|---|---|---|---|---|---|---|---|---|
| C10WBA-IgG23_26 | 9 | 0.624 | 0.5 | VHH | 5 | 0.48 | 0.5 | 26 |
| C10WBA-IgG23_26 | 8 | 0.68 | 0.5 | VHH | 5 | 0.464 | 0.5 | 26 |

Specific antibody each has a sequence as shown below:

>C10WBA-IgG23_26
(SEQ ID NO: 21)
MAHVQLVESGGGSVQAGGSLKLSCAVSPYIFTRCGLGWYRQAPGNVRELV
SSMDSDGTTIYADSVKGRFTISQDNEKNMLYLQMNSLKTEDTAMYYCAAD
HQDPSRGAYFDHCNYMGQGTQVTVS

>C10WBA-IgG23_1064
(SEQ ID NO: 22)
MADVQLVESGGGLVQPGGSLRLSCVGSGFGPKVYCMGWFRQAPGKEREG
VAAVDSEGNTSYVESVKGRFTISQDKDKNTVYLEMNNLKPEDTAMYYCA
AELQIPLNRQVAGRSWHCPLLAPVSAGGRHSGVWGQGTQVTVS

>C10WBA-IgG23_666
(SEQ ID NO: 23)
MADVQLVESGGGSVQAGGSLRLSCSISPAISHRNCMAWFRQVPGNEREG
VAAIYLTAGATHYIDSVKGRFTISEDSAENTMYLQMENLKSEDTGMYYC
AADFFPFKGGAASLAPMCLNGLEYRHRGQGTQVTVS

Example 3

Nanobody was synthesized in accordance with the gene sequence of antibody obtained in Example 1 by screening, and expressed via a protein expression system for identification.

I. Constructing an Expression Vector
1. Digestion

20 µl plasmid pET28a DNA was digested with 1 µl EcoRI and 1 µl BamHI at 37° C. for 5 h along with 5 µl 10×K buffer and 23 µl ddH₂O. Targeting fragments (i.e. gene sequence of the nanobody) and vectors were retrieved by a commercial kit for extracting DNA after agarose gel electrophoresis.

2. ligation and transformation
2.1 ligation

1 µl vector, 3 µl targeting fragments, 1 µl T4 ligase, 5 µl 2×buffer were mixed to be uniform and reacted for more than 30 min, thereby obtaining a ligation product.

2.2 transformation 2.2.1 Competent cells (BL21) reserved at −80° C. were thawed on ice slowly.

2.2.2 The thawed competent cells were added into the ligation product or plasmid DNA (1 µl), followed by mixed to be uniform and placed on ice for 30 mM, thereby obtaining a first mixture.

2.2.3 The first mixture obtained was heat shocked at 42° C. for 90 seconds, thereby obtaining a second mixture.

2.2.4 After incubated in an ice-bath for 2 mM, the second mixture obtained was added into 800 µl LB medium without antibiotics, thereby obtaining a third mixture.

2.2.7 After dried by air, the resulting plate was inverted and incubated at 37° C. in an incubator over night.

3. Selecting and culturing single colony 3.1 one well-isolated transformed colony from the plate obtained in the previous step was transferred to 1.5 ml liquid LB medium, and then incubated at 37° C. in a shaking incubator at a speed of 200 rpm, until this incubating solution was of an OD value of 0.6 to 0.8 in spectrophotometer, thereby obtaining seed liquid.

3.2 The seed liquid cultured by 1.5 ml LB medium was then transferred to 1 L scale-up medium, and continuously incubated until this incubating solution was of an OD value of 0.6 to 0.8 (indicating logarithmic growth phase) in spectrophotometer. At this time, IPTG (0.5 mM) was added therein for induction, followed by incubation at 37° C. for 2 hours in a shaking incubator at a speed of 200 rpm.

3.3 Bacterial solution collected was centrifuged at 13200 r/min for 15 mM. After discarding resulting supernatant, resulting pellet was washed by addition of 0.01 mol/L PBS, thereby obtaining a resuspending solution. The resuspending solution was centrifuged again, to obtain pellet for storage in −80° C.

4. Protein sample collection and purification on a nickel column 4.1 lysing the bacterial pellet on ice with 2 ml to 5 ml of lysis buffer per gram, followed by sufficient resuspension;

4.2 adding lysozyme till having a final concentration of 1 mg/ml, followed by mixed to be uniform and placed on ice for 30 min;

4.3 subjecting to ultrasound at 200 to 300 W for six times with an interval of 10 seconds, each time lasting 10 seconds;

4.4 adding RNaseA (10 ug/ml) and DNase (5 ug/ml), followed by placed on ice for 10 min to 15 min;

4.5 centrifuging at 10000 r/min for 20 min to 30 min at 4° C., followed by collecting supernatant which was then filtered with 0.45 mm filter membrane;

4.6 packing a column with 2 ml Ni-NTA agarose resin; 4.7 sufficiently equilibrating the Ni-NTA agarose resin column by slow addition of an equilibrium solution having a volume 10 times of the Ni-NTA agarose resin column at a flow rate of 1 ml/min;

4.8 loading all lysed bacterial solution after filtration onto the Ni-NTA agarose resin column at a constant speed; then washing the Ni-NTA agarose resin column with the equilibrium solution having a volume 10 times of the Ni-NTA agarose resin column with a flow rate held at 1 ml/min;

4.9 stepwise eluting with an elution solution having an imidazole concentration of 50 mmol/L, 100 mmol/L and 200 mmol/L at a flow rate of 2 ml/min, followed by collecting eluents in separate tubes with individual marker in sequence, respectively, each having a volume of 1 ml.

5. SDS-polyacrylamide gel electrophoresis (PAGE)

Figure 14:
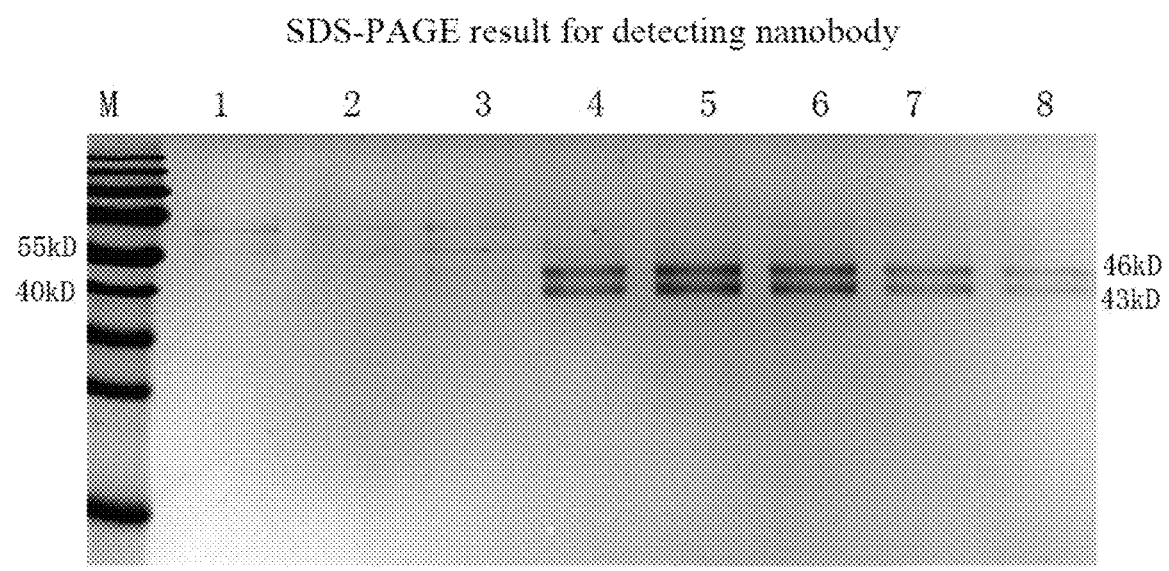
FIG. 14 is an SDS-PAGE result for detecting molecular weight of screened nanobody in an embodiment of the present disclosure.

The protein sample was added with 2×loading buffer at a volume ratio of 1:1, thereby obtaining a loading sample. After incubated at 100° C. for 5 min, the loading sample was subjected to SDS-PAGE, thereby obtaining a result as shown in FIG. 14.

II. Identification of Antibody

The antibody obtained was identified by ELASA method with the following steps:

After subjected to ultrasonic, the bacterial solution collected after induction in step 3.2 (i.e., proteins with low expression) was centrifuged at 12000 rpm for 10 min. The resulting supernatant was transferred to a new EP tube, used as antibody sample.

1. Coating:

Each well of the ELISA plate was coated with antigen polypeptide for conjugation having a concentration of 10 μg/ml at 4° C. over night. Duplicate wells after coated were reserved for each sample.

2. Blocking:

The ELASA plate after coated was washed three times in microplate washer. After dried with absorbent paper, the ELASA plate was blocked with 1% BSA (200 μl/well) at 4° C. over night or 37° C. for 2 hours.

3. Addition of primary antibody

After blocked with 1% BSA, the ELASA plate was washed three times in microplate washer, followed by dried with absorbent paper. Depending on different experiments, primary antibody (i.e., supernatant of protein with low expression and purified antibody) was added into corresponding selected plate, followed by incubation at 37° C. for 2 hours.

4. Plate washing

The resulting plate was washed five times or more in microplate washer, followed by dried with absorbent paper.

5. Addition of secondary antibody

The wells containing supernatant of protein with low expression were added with His antibody with 1:2000 dilution as the secondary antibody, and the rest of wells were added with PBS. The plate was then incubated at 37° C. for 1 hour.

6. Plate washing

The resulting plate was washed five times or more in microplate washer, followed by dried with absorbent paper.

7. Developing

A developing solution (TMB) and a stopping solution were prepared for use. Each well of the plate was added with 100 μl developing solution. The developing process could be sped up by shaking the plate. Each well was added with 50 μl stop solution when the developing was achieved to a certain extent (it should be controlled generally that color for blank and negative control cannot be over developed), followed by placed for 10 min or more for thorough stopping developing reaction and uniform color (the stopping process could be sped up by shaking the plate).

8. Reading

After reaction was stopped, the plate were subjected to spectrophotometric assays on microplate reader at a detection wavelength of 450/630 for TMD developing, which had been heated for 30 mine in advance.

Under a certain dilution (eg. 1:10), the nanobody having an OD value 1.5 times or more of the negative control (i.e., PBS control) is considered to be active. In the case that PBS control has an OD value of 0.117, then the nanobody having an OD value greater than 0.175 (0.117×1.5) is considered to be active. All results are shown in the table below. Sequences with individual marker such as 11-1A and 22-2B which were obtained by screening in Example 2, eg. >C10WBA-IgG23_26, were expressed by the steps described in Example 3. In this example, 22-2B, 12-1B, 31-3A were identified as positive antibody.

| Coated antibody 1 μg/well | primary antibody 11-1A (1:10) | 11-1A (1:100) | 11-1A (1:1000) | 12-1B (1:10) | 12-1B (1:100) | 12-1B (1:1000) |
|---|---|---|---|---|---|---|
| | 0.165 | 0.102 | 0.084 | 0.214 | 0.119 | 0.075 |
| | primary antibody 22-2B (1:10) | 22-2B (1:100) | 22-2B (1:1000) | 31-3A (1:10) | 31-3A (1:100) | 31-3A (1:1000) |
| | 0.258 | 0.098 | 0.071 | 0.454 | 0.155 | 0.080 |
| Coated antibody 1 μg/well | primary antibody 11-1A (1:10) | 11-1A (1:100) | 11-1A (1:1000) | 12-1B (1:10) | 12-1B (1:100) | 12-1B (1:1000) |
| | 0.174 | 0.134 | 0.079 | 0.321 | 0.132 | 0.074 |
| | primary antibody 22-2B (1:10) | 22-2B (1:100) | 22-2B (1:1000) | 31-3A (1:10) | 31-3A (1:100) | 31-3A (1:1000) |
| | 0.236 | 0.098 | 0.082 | 0.439 | 0.172 | 0.083 |
| Coated antibody 1 μg/well | 13-1C (1:10) | 13-1C (1:100) | 13-1C (1:1000) | 21-2A (1:10) | 21-2A (1:100) | 21-2A (1:1000) |
| | 0.137 | 0.096 | 0.129 | 0.111 | 0.094 | 0.112 |
| | 31-3B (1:10) | 31-3B (1:100) | 31-3B (1:1000) | PBS control | 72676 (1:100) | 72676 (1:1000) |
| | 0.139 | 0.133 | 0.120 | 0.107 | 0.575 | 0.173 |
| Coated antibody 1 μg/well | 13-1C (1:10) | 13-1C (1:100) | 13-1C (1:1000) | 21-2A (1:10) | 21-2A (1:100) | 21-2A (1:1000) |
| | 0.178 | 0.107 | 0.114 | 0.117 | 0.115 | 0.133 |
| | 31-3B (1:10) | 31-3B (1:100) | 31-3B (1:1000) | PBS control | 72829 (1:100) | 72829 (1:1000) |
| | 0.164 | 0.153 | 0.134 | 0.117 | 1.679 | 1.561 |

Reference throughout this specification to "an embodiment", "some embodiments", "one embodiment", "another example", "an example", "a specific example", or "some examples" means that a particular feature, structure, material, or characteristic described in connection with the embodiment or example is included in at least one embodiment or example of the present disclosure. Thus, the appearances of the phrases such as "in some embodiments", "in one embodiment", "in an embodiment", "in another example", "in an example", "in a specific example", or "in some examples" in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A method for screening a nanobody, comprising the following steps:
   (1) extracting a nucleic acid sample from tissue or peripheral blood obtained from an animal after immunized;
   (2) obtaining a sequencing result containing an antibody sequence based on the nucleic acid sample;
   (3) constructing an antibody database based on the sequencing result containing the antibody sequence, wherein the step (3) comprises sub-steps of:
      (3a) aligning the sequencing result containing the antibody sequence to a reference sequence to determine an immune-related gene sequence,
      (3b) determining a nucleotide sequence of the antibody based on the immune-related gene sequence,
      (3c) translating the nucleotide sequence of the antibody into an amino acid sequence, and
      (3d) screening to obtain a VHH sequence based on the amino acid sequence, and constructing the antibody database;
   (4) subjecting the antibody database to information analysis, to obtain sequence of the nanobody;
   (5) subjecting serum obtained from the animal after immunized to protein mass spectrometry analysis to obtain a result of protein mass spectrometry;
   (6) integrating information of the antibody database with the result of protein mass spectrometry for analysis to obtain the sequence of the nanobody; and
   (7) expressing the nanobody via a protein expression system based on the sequence of the nanobody, to identify the nanobody.

2. The method according to claim 1, wherein the animal is a Camelidae family animal.

3. The method according to claim 2, wherein the Camelidae family animal is at least one selected from *Camelus dromedarius, Camelus bactrianus, Lama guanicoe, Lama glama, Vicugna vicugna*, and *Vicugna pacos*.

4. The method according to claim 1, wherein the step (5) further comprises:
   (5a) enriching IgG from the serum of the animal after immunized with Protein A/G to obtain an enriched product;
   (5b) affinity purifying, by a chromatographic column conjugated with the antigen, the antibody from the enriched product to obtain a purified product;
   (5c) subjecting the purified product to denaturation and reductive alkylation, and then lysing with protease to obtain an enzyme-digested peptide; and
   (5d) subjecting the enzyme-digested peptide to protein mass spectrometry analysis on mass spectrometer to obtain a mass spectrometry result of the enzyme-digested peptide.

5. The method according to claim 4, wherein the protease is at least one of pepsin, chymotrypsin, elastinase, trypsin, endoproteinase Lys-C, metalloendopeptidase Lys-N, endoproteinase Glu-C, aspartate endopeptidase Asp-N, and clostripain Arg-C.

6. The method according to claim 1, wherein the antibody sequence includes a hypervariable region and a framework region.

7. The method according to claim 1, wherein the nucleic acid sample is DNA or RNA.

8. The method according to claim 1, wherein in the case that the nucleic acid sample is DNA, the antibody sequence in the nucleic acid sample is amplified by polymerase chain reaction (PCR); in the case that the nucleic acid sample is RNA, the antibody sequence in the nucleic acid sample is amplified by 5'-rapid amplification cDNA ends (5'-RACE) or PCR.

9. The method according to claim 8, wherein the PCR is at least one of multiplex PCR, linear amplification mediated PCR, and nested PCR.

10. The method according to claim 1, wherein the amplification product is sequenced on a high-throughput sequencing device.

11. The method according to claim 1, wherein the immune-related gene sequence is at least one selected from a V gene, a D gene, a J gene and a C gene.

12. The method according to claim 1, wherein the reference sequence is a known germline sequence in the absence of rearranging at least one of the V gene, the D gene, the J gene and the C gene.

13. The method according to claim 1, wherein in the sub-step (3d), an indicator of determining the amino acid sequence to be the VHH sequence comprises at least one of:
   A: a presence of any one of four conserved amino acids: 37F, 44E, 45R and 47G,
   B: a presence of sequences shown as SEQ ID NO: 1 and SEQ ID NO: 2 in a hinge region, and
   C. absence of at least one portion of CH1.

14. The method according to claim 1, wherein the step (2) further comprises the following sub-steps:
   (2a) amplifying the antibody sequence in the nucleic acid sample to obtain an amplification product; and
   (2b) subjecting the amplification product to sequencing to obtain the sequencing result containing the antibody sequence.

* * * * *

UNITED STATES PATENT AND TRADEMARK OFFICE
CERTIFICATE OF CORRECTION

PATENT NO. : 10,954,550 B2
APPLICATION NO. : 15/502438
DATED : March 23, 2021
INVENTOR(S) : Xiao Liu et al.

Page 1 of 1

It is certified that error appears in the above-identified patent and that said Letters Patent is hereby corrected as shown below:

On the Title Page

Item (73) Assignee, delete "BGI SHENZHEN" and add --BGI SHENZHEN CO., LIMITED--

Signed and Sealed this
Twenty-sixth Day of September, 2023

Katherine Kelly Vidal
*Director of the United States Patent and Trademark Office*